United States Patent [19]

Lynn et al.

[11] Patent Number: 5,643,218
[45] Date of Patent: Jul. 1, 1997

[54] AUTO-FLUSHING MEDICAL FLUID INJECTION SYSTEM

[75] Inventors: Lawrence A. Lynn, 862 Curleys Ct., Columbus, Ohio 43235; Mark E. Larkin, Columbus, Ohio

[73] Assignee: Lawrence A. Lynn, Columbus, Ohio

[21] Appl. No.: 697,058

[22] Filed: Aug. 20, 1996

Related U.S. Application Data

[62] Division of Ser. No. 413,966, Mar. 30, 1995, Pat. No. 5,549,569, which is a division of Ser. No. 196,455, Feb. 15, 1994, abandoned.

[51] Int. Cl.$^6$ ...................................... A61M 5/00
[52] U.S. Cl. ............... 604/191; 604/89; 604/207; 128/762; 128/760
[58] Field of Search ............... 604/89–91, 187, 604/191, 207–208, 218, 238, 122–125; 128/760, 762

[56] References Cited

U.S. PATENT DOCUMENTS

| | | |
|---|---|---|
| 2,357,238 | 8/1944 | Trimble . |
| 2,847,996 | 8/1958 | Cohen . |
| 2,922,420 | 1/1960 | Cheng . |
| 2,989,053 | 6/1961 | Hamilton . |
| 3,067,742 | 12/1962 | Linke . |
| 3,291,151 | 12/1966 | Loken . |
| 3,344,785 | 10/1967 | Hamilton . |
| 3,494,359 | 2/1970 | Zackheim . |
| 3,511,239 | 5/1970 | Tuschhoff . |
| 3,563,240 | 2/1971 | Silver . |
| 3,680,558 | 8/1972 | Kapelowitz . |
| 3,730,170 | 5/1973 | Michael . |
| 3,807,119 | 4/1974 | Shields . |
| 3,835,835 | 9/1974 | Thompson . |
| 3,835,855 | 9/1974 | Barr, Jr. . |
| 3,985,122 | 10/1976 | Topham . |
| 4,013,064 | 3/1977 | Patel . |
| 4,014,328 | 3/1977 | Cluff et al. . |
| 4,051,852 | 10/1977 | Villari . |
| 4,058,121 | 11/1977 | Choksi . |
| 4,197,848 | 4/1980 | Garrett et al. . |
| 4,214,779 | 7/1980 | Losell . |
| 4,219,021 | 8/1980 | Fink . |

(List continued on next page.)

FOREIGN PATENT DOCUMENTS

| | | |
|---|---|---|
| 1394570 | 4/1970 | Australia . |
| 0050459 | 10/1981 | European Pat. Off. . |
| 0111723 | 11/1983 | European Pat. Off. . |
| 0208975 | 1/1987 | European Pat. Off. . |
| 1373027 | 8/1963 | France . |
| 2049513 | 3/1971 | France . |
| 2439022 | 10/1979 | France . |
| 9201485 | 6/1992 | WIPO . |

OTHER PUBLICATIONS

Catalog, American Scientific Products, p. 1568, 1987–88.
Introducer Kit, Arrow International.
Intravenous Tubing Set (Terminal At One End).
Silver et al. Evaluation of a New Blood–Conserving Arterial Line System for Patients in Intensive Care Units, Critical Care Medicine, vol. 21, No. 4, 1993. pp. 507–511.

*Primary Examiner*—Vincent Millin
*Assistant Examiner*—Perry E. Van Orer
*Attorney, Agent, or Firm*—Cushman Darby & Cushman Intellectual Property Group of Pillsbury Madison & Sutro, LLP

[57] ABSTRACT

A syringe for the sequential withdrawal of a first liquid and a second liquid. The syringe has a barrel, a proximal piston moveable along the barrel to define a variable volume chamber intermediate the piston and the end of the barrel, and a distal chamber divider piston for separating the variable volume chamber into primary and secondary reservoirs. A flow channel is defined along the syringe for providing flow connection between the primary and secondary reservoirs. An element links the two pistons so that as the proximal piston is moved away from the distal piston, the first liquid enters the first reservoir and thereafter the second liquid enters the secondary reservoir.

8 Claims, 13 Drawing Sheets

U.S. PATENT DOCUMENTS

| | | |
|---|---|---|
| 4,276,880 | 7/1981 | Malmin . |
| 4,335,717 | 6/1982 | Bujan . |
| 4,364,383 | 12/1982 | Vcelka . |
| 4,437,858 | 3/1984 | Ty . |
| 4,439,184 | 3/1984 | Wheeler . |
| 4,453,934 | 6/1984 | Gahwiler . |
| 4,464,174 | 8/1984 | Ennis . |
| 4,496,344 | 1/1985 | Kamstra . |
| 4,496,350 | 1/1985 | Cosentino . |
| 4,578,063 | 3/1986 | Inman et al. . |
| 4,588,403 | 5/1986 | Weiss et al. . |
| 4,601,703 | 7/1986 | Herlitze . |
| 4,609,371 | 9/1986 | Pizzino . |
| 4,610,666 | 9/1986 | Pizzino . |
| 4,634,427 | 1/1987 | Hannula . |
| 4,645,491 | 2/1987 | Evans . |
| 4,650,468 | 3/1987 | Jennings . |
| 4,650,475 | 3/1987 | Smith . |
| 4,654,034 | 3/1987 | Masters . |
| 4,655,747 | 4/1987 | Allen, Jr. . |
| 4,666,438 | 5/1987 | Raulerson . |
| 4,673,386 | 6/1987 | Gordon . |
| 4,675,004 | 6/1987 | Hadford . |
| 4,675,005 | 6/1987 | De Luccia . |
| 4,675,007 | 6/1987 | Terry . |
| 4,675,017 | 6/1987 | Sato . |
| 4,685,904 | 8/1987 | Krebs . |
| 4,693,706 | 9/1987 | Ennis, III . |
| 4,699,612 | 10/1987 | Hamacher . |
| 4,702,737 | 10/1987 | Pizzino . |
| 4,710,180 | 12/1987 | Johnson . |
| 4,715,854 | 12/1987 | Vaillancourt . |
| 4,721,506 | 1/1988 | Teves . |
| 4,752,292 | 6/1988 | Lopez et al. . |
| 4,758,225 | 7/1988 | Cox . |
| 4,759,756 | 7/1988 | Forman . |
| 4,763,648 | 8/1988 | Wyatt . |
| 4,776,843 | 10/1988 | Martinez . |
| 4,792,329 | 12/1988 | Schreuder . |
| 4,796,644 | 1/1989 | Polaschegg . |
| 4,799,494 | 1/1989 | Wang . |
| 4,830,013 | 5/1989 | Maxwell . |
| 4,834,152 | 5/1989 | Howson . |
| 4,834,714 | 5/1989 | Lascar . |
| 4,838,855 | 6/1989 | Lynn . |
| 4,838,877 | 6/1989 | Massau . |
| 4,865,583 | 9/1989 | Tu . |
| 4,911,705 | 3/1990 | Heinzerling et al. . |
| 4,920,970 | 5/1990 | Wyatt . |
| 4,932,944 | 6/1990 | Jagger . |
| 4,941,876 | 7/1990 | Meyer . |
| 4,979,941 | 12/1990 | Ogle . |
| 4,979,942 | 12/1990 | Wolf . |
| 4,981,140 | 1/1991 | Wyatt . |
| 4,986,278 | 1/1991 | Ravid . |
| 4,989,606 | 2/1991 | Gehrich . |
| 4,994,043 | 2/1991 | Ysebaert . |
| 5,007,903 | 4/1991 | Ellard . |
| 5,048,537 | 9/1991 | Messinger . |
| 5,078,691 | 1/1992 | Hamacher . |
| 5,102,388 | 4/1992 | Richmond . |
| 5,125,892 | 6/1992 | Drudik . |
| 5,147,323 | 9/1992 | Haber . |
| 5,158,554 | 10/1992 | Jepson et al. . |
| 5,324,266 | 6/1994 | Ambrisco et al. . |
| 5,429,610 | 7/1995 | Vaillancourt . |

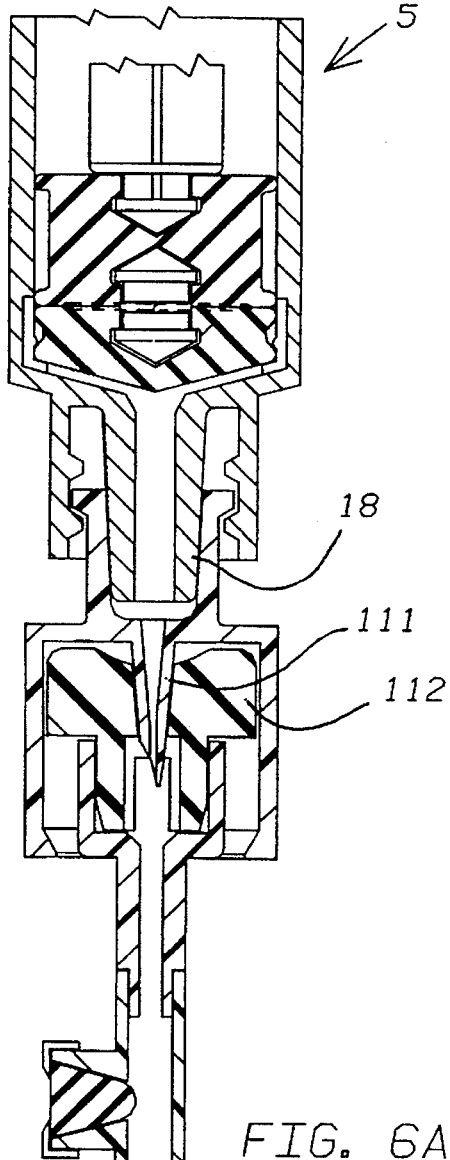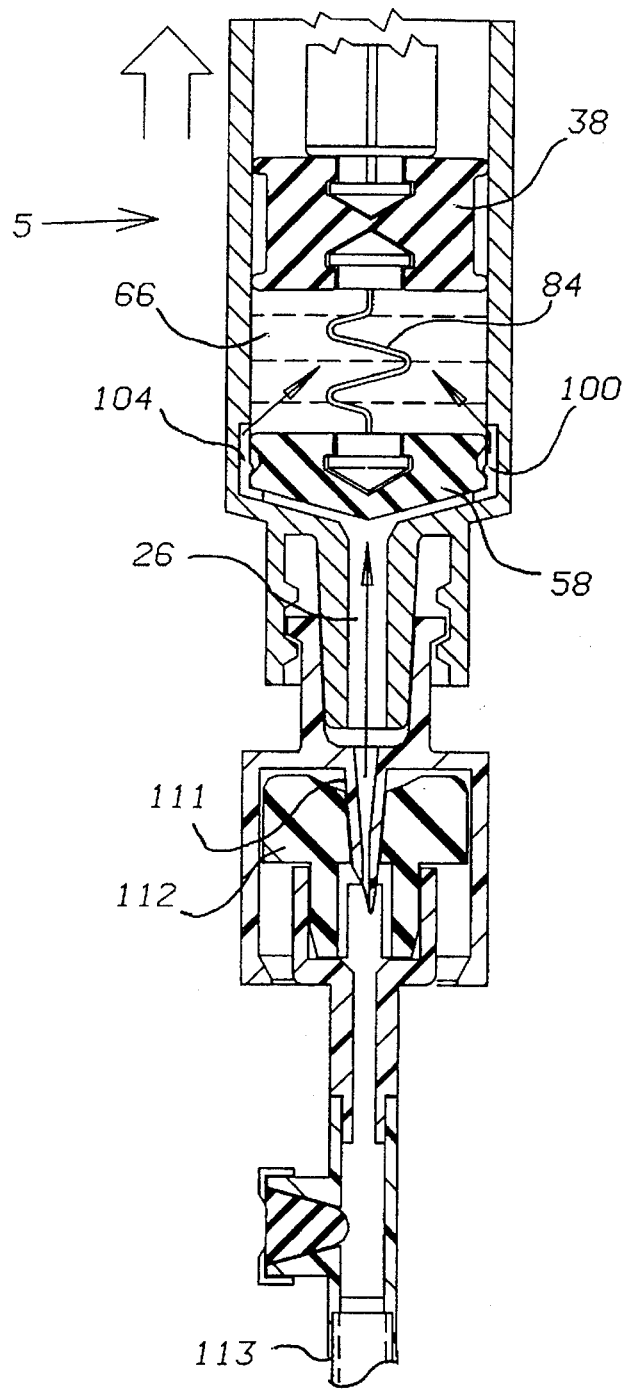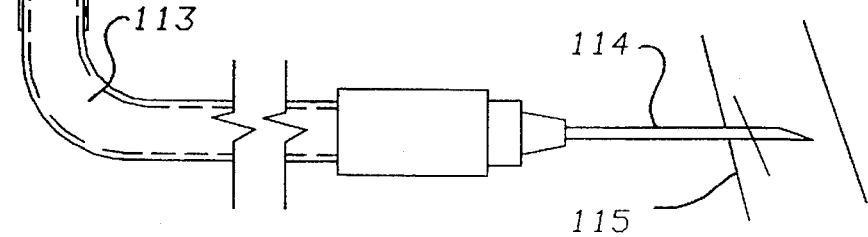
FIG. 6A    FIG. 6B

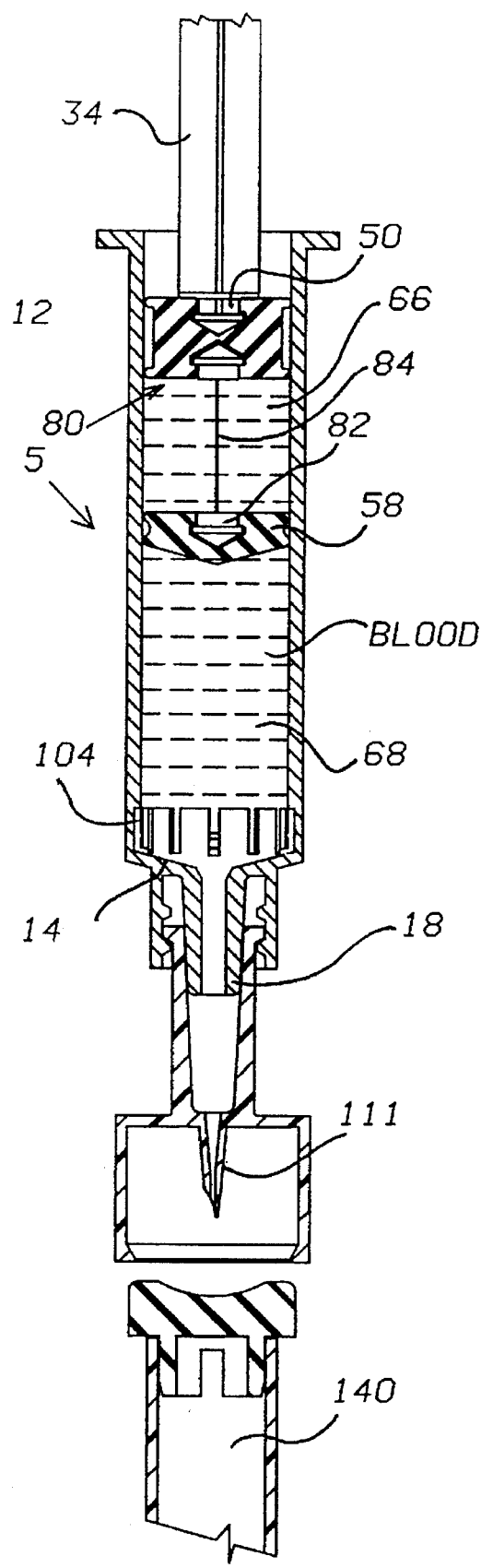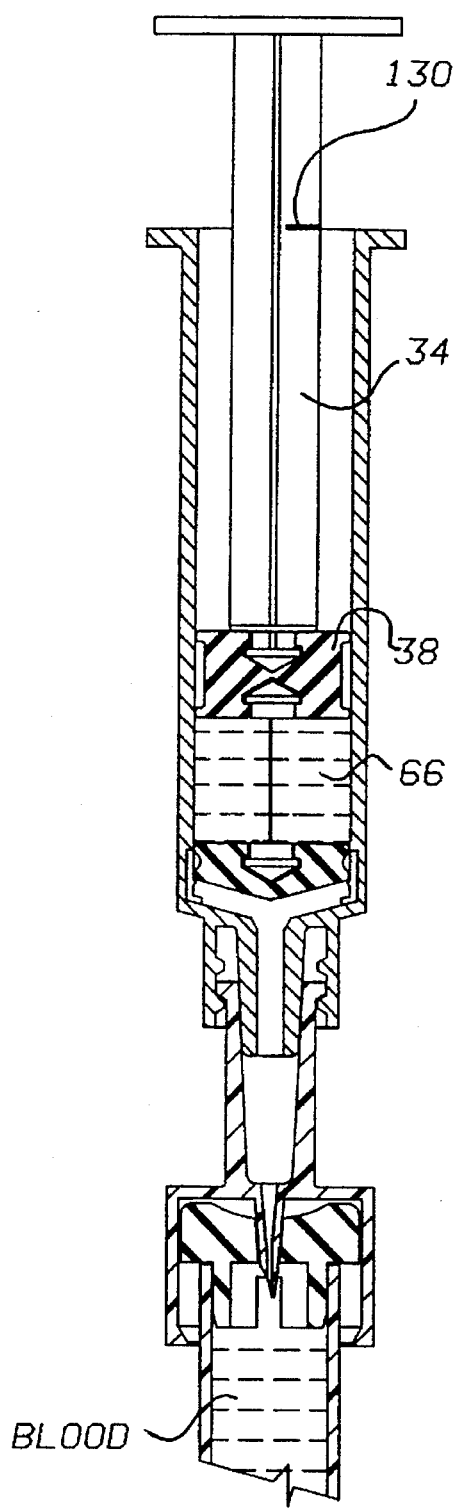
FIG. 6C
FIG. 7

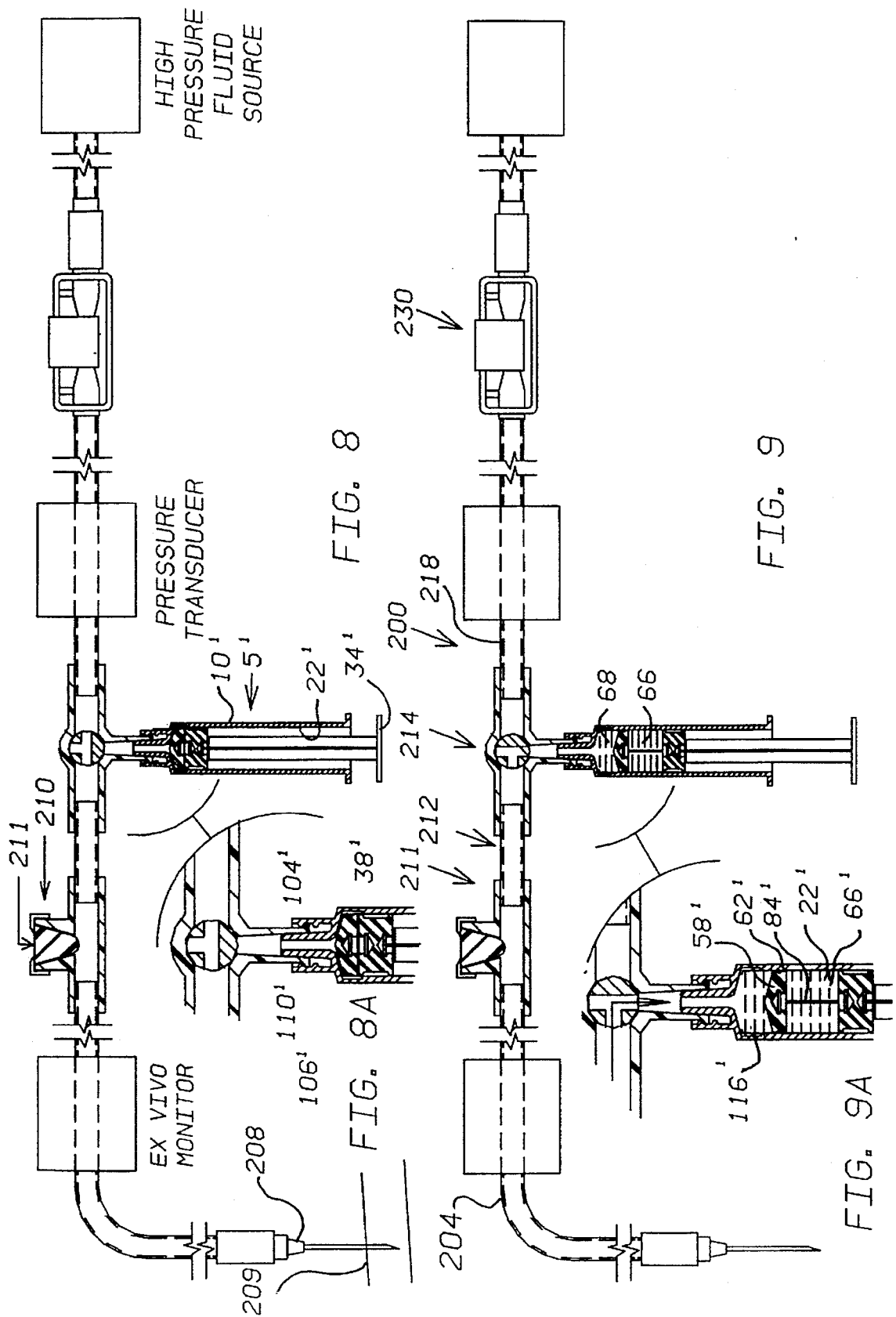

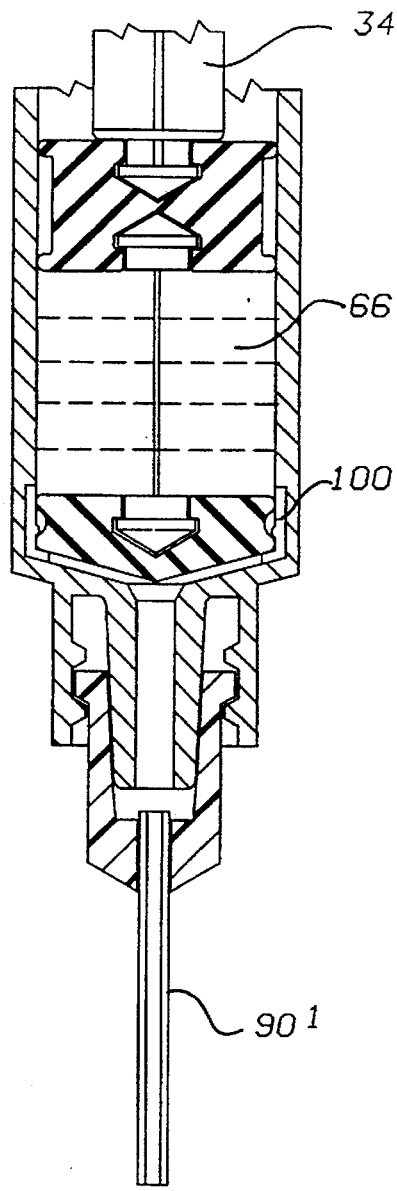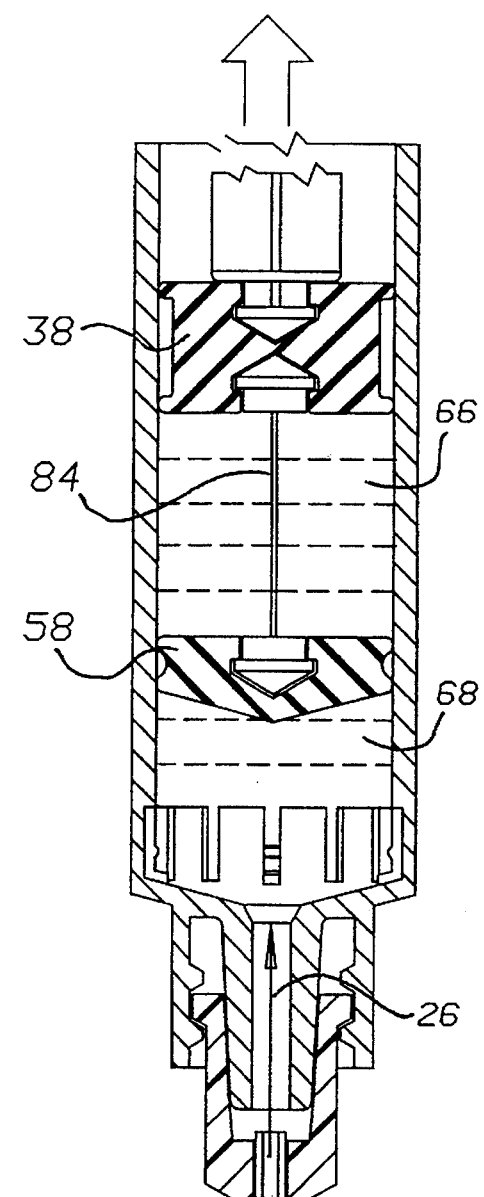
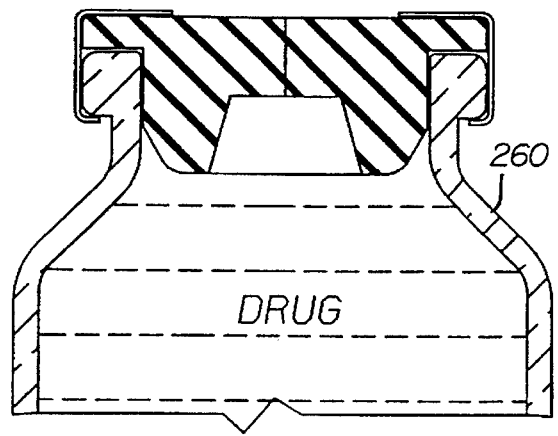
FIG. 12
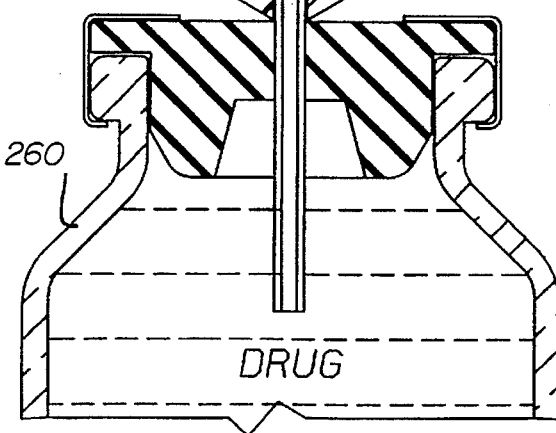
FIG. 13

AUTO-FLUSHING MEDICAL FLUID INJECTION SYSTEM

BACKGROUND AND SUMMARY OF THE INVENTION

This is a division of application Ser. No. 08/413,966, filed Mar. 30, 1995 now U.S. Pat. No. 5,549,569 which was a Division of Ser. No. 08/196,455 filed Feb. 15, 1994, now abandoned.

Intravenous drugs are commonly administered utilizing injection through a self-sealing port, including y-adapters and prn adapters (also called saline wells or heparin wells). These intravenous systems commonly include deadspace which must be flushed free of the injected drug after the drug injection so that drug incompatibility will not occur with sequential injections of different drugs. Drugs are commonly injected in solution utilizing a conventional syringe with a needle or blunt cannula attached to the end for injection through the port. After the injection, however, a second syringe filled with saline must be inserted through the port to flush any residual drug solution from the deadspace of the tubing so that residual drug solution does not remain in this deadspace to prevent the potential for drug incompatibility should another drug be injected in the future through this same port. The nurse, therefore, draws up the drug with its solution into a first syringe and draws saline into a second syringe. The nurse commonly injects the drug solution through the port and into the patient, then injects the saline through the port to flush the drug from the deadspace of the system. Because sharp needles have been associated with significant infection risk to hospital personnel, it is common to utilize blunt or protected cannulas to provide safety during such injections. Since, as discussed, two injections are required to assure that the drug does not remain within the deadspace, the nurse must commonly utilize two separate syringes and two separate cannulas, resulting in considerable expense. Furthermore, multiple injections increase the risk of infection to the patient and, since such ports are commonly connected closely with an indwelling catheter, the greater the number of such injections, the greater the potential for manipulation of the catheter, which can result in thrombosis of the vein. In addition, multiple injections result in increase in exposure of hospital personnel to potentially infectious liquids from the patient and increase the amount of time spent in delivering drugs to the patient.

Given the aforementioned problem, there has long been a need for a system which can allow the nurse to inject a drug solution and subsequently flush the deadspace of the tubing or catheter utilizing the same syringe, thereby eliminating the need for multiple entries into the port and its associated problems.

An additional problem exists with automatic infusion devices which utilize syringes. These devices are commonly used for injection of medication into patients and do not require close attention by hospital personnel. However, once the infusion of these devices is complete, the drug may remain within the patient's vein and the deadspace of the tubing if the hospital personnel do not promptly arrive to flush the drug from these areas with saline solution. This can result in potential injury to the patient's vein, thrombosis, precipitation of the drug within the tubing, or chemical incompatibility and precipitation if another nurse fails to recognize the presence of drug within the tubing and injects a different incompatible drug into the tubing system. There is, therefore, a need for a system which can automatically flush the tubing after an injection whether or not the injection is provided by the nurse or a mechanical or electronic infusion device. This would allow more safe unattended injection by mechanical devices in the home setting. U.S. Pat. No. 4,857,056 describes a system for providing automatic infusion of a drug followed by a flush solution. This device, however, requires the provision of two syringes and many mechanical and electronic infusion devices are designed to interface with a single syringe. Furthermore, two syringes result in additional expense when compared with a single syringe system.

As hospital costs increase, it has become desirable to reuse disposable medical equipment for the same patient for short periods of time (for example, 24–96 hours). It is, therefore, advantageous to provide a multiple use syringe for use with a single patient over multiple aspirations and injections of sequential medication. U.S. Pat. No. 4,439,184 discloses a single syringe for the injection of two different drugs. The syringe has proximal and distal chambers and two pistons and a proximal no-pass region and a distal by-pass region. However, this syringe can only provide a single sequential injection from each compartment since there is no provision for withdrawing the distal piston from the by-pass region for sequential fluid withdrawal or for presetting the volume of the proximal chamber during the withdrawal maneuver. Therefore, there is no provision for allowing the nurse to easily aspirate the respective solutions into the syringe. There are numerous additional multi-chambered syringes in the prior art: U.S. Pat. No. 5,102,388 discusses a multi-chamber syringe for sequential injection of different drug solutions. Piercing devices are disclosed which sequentially pierce stoppers during the injection; U.S. Pat. No. 5,125,892 discloses a multi-chambered syringe having a hollowed dilated piston which can burst; U.S. Pat. No. 4,655,747 discloses a dual-chambered syringe having an inner and outer barrel; U.S. Pat. No. 4,610,666 discloses a tandem barrel syringe; U.S. Pat. No. 4,496,344 discloses a multiple compartment syringe having a distal bypass region; U.S. Pat. No. 4,464,174 discloses a two-compartment mixing syringe with an inner and outer barrel; U.S. Pat. No. 4,453,934 discloses a piston having a distal container which can fracture for the sequential delivery of, for example, a contrast agent followed by a saline flush solution; U.S. Pat. No. 3,985,122 discloses a syringe having two bores and two pistons having different diameters for mixing solutions within the syringe; U.S. Pat. No. 3,807,199 discloses a method for assembling a multiple compartment syringe and for preloading the syringe with a measured quantity of liquid; U.S. Pat. No. 3,494,359 discloses a two-compartment syringe utilizing a compartment separator which can deflect for mixing of the solution; U.S. Pat. No. 3,511,239 discloses a two-compartment syringe having two pistons and a rod extending through the pistons with a longitudinal bore which provides communication between the two chambers, allowing the fluid in the upper chamber to be mixed with the drug in the lower chamber; U.S. Pat. No. 4,792,329 describes a mixing syringe having a bypass region and three separate stoppers for mixing and subsequently injecting two solutions; U.S. Pat. No. 4,693,706 describes a mixing syringe having inner and outer cylindrical barrels for mixing two solutions; U.S. Pat. No. 4,834,714 describes a double barrel arrangement capable of achieving the double capacity of a single syringe; U.S. Pat. No. 3,680,558 discloses a multiple compartment syringe having telescoping barrels with an intermediate valve which can be opened by rotation; PCT Application WO92/01485 discloses a syringe having a barrel with a cylindrical insert for long-ten storage and subsequent mixing and injection of two drugs. In addition to the foregoing discussion, the above patents provide additional general background of this invention. Importantly, multi-barrel syringes are associated with additional expense and complexity whether in tandem or telescopic configuration. Also, it is expensive to preload a multi-compartment syringe with flush solution and pre-loading may require the addition of glass or other containers to maintain stability of the solution, which adds additional expense. To achieve reduction in cost, it would be advantageous for the nurse to aspirate a specific preset quantity of flush solution into the syringe immediately prior to use. It would further be advantageous for the volume of this flush solution to be preset by an indicator so that the nurse is confident that adequate flush volume is present to completely flush the deadspace of the syringe and the deadspace of conventional wells when it has been indicated by the indicating means that the syringe contains adequate flush volume. The present invention functions to achieve these and other advantages, as will become evident from the following discussion and claims.

Another common problem relates to blood sampling. Syringes have been commonly used to draw blood out of intravenous lines or arterial lines. However, such blood is commonly diluted with the saline or heparin solution which generally dwells within the deadspace of the intravenous or arterial line. Problems related to blood collection are described in U.S. Pat. No. 3,835,835, which discloses a multi-barrel two-compartment syringe for collecting a pure uncontaminated blood specimen. Another system for isolating pure blood is discussed in my U.S. Pat. No. 4,838,855 (the disclosure of which is hereby incorporated by reference as if completely disclosed herein). This patent describes a system and method for repetitively achieving an undiluted specimen of blood outside a patient for testing or sampling. The system utilizes a variable volume reservoir and predetermined volumes to separate the fluid which is indwelling within the robing system from the blood and fluid mixture that naturally occurs upon withdrawal of blood into the robing. This allows the stored fluid within the syringe which is not contaminated with blood to be utilized to flush blood from the system after blood testing or sampling. This system has the important advantage of providing for the separation and isolation of a portion of the original fluid stored within the deadspace of the tubing from the blood that is withdrawn into the system so that the isolated fluid can later be used to flush the blood from the tubing, thereby providing ease of operation and reducing the risk of accumulation of blood within the deadspace of the reservoir. The system also minimizes the amount of total fluid added to the system and the patient during repetitive sampling or testing.

Commonly, however, it is necessary to draw blood at substantial distances from the indwelling catheter, such as during anesthesia when the anesthesiologist is sitting at the head of the bed above the head of the patient and wherein the patient is draped by sterile drapes for surgery. A radial artery catheter is positioned in an arm, which often is directed downward at the side of the patient. Therefore, the anesthesiologist is required to sample blood at the head of the bed from an arm positioned near the patient's hip so that the distance may be substantially greater than 1 meter. In such situations, it would advantageous to store the blood and fluid mixture within a syringe reservoir, rather than solely within the tubing itself, since the length of the tubing is so great between the patient and the sampling site that a large volume of blood must be drawn into the system to adequately clear the line at the sampling site. Furthermore, it is commonly necessary to draw blood from indwelling catheters that do not have fixed reservoirs attached, such as multilumen catheters. Such catheters commonly do not conventionally have adequate tubing length to provide the capacitance storage function described in my aforementioned patent.

In addition to these problems, it would be advantageous not to leave certain toxic drugs or radioactive materials within the deadspace of a syringe or cannula or heparin well after an injection. This is particularly true with the injection of chemotherapeutie drugs which may be highly toxic to the nurse providing the injection if the nurse is exposed to even minute quantities of the drug over a sustained period of time. An injection of a chemotherapeutic agent through a cannula and then the withdrawal of that cannula can remit in minute quantities of the chemotherapeutie agent being expelled in the region around the injection sight or in the environment prior to dropping the cannula and/or syringe within the waste receptacle. This is also true of radioactive materials which are commonly injected (for example, during an exercise stress test) at a time wherein minute quantities are best completely injected into the patient so that there is less potential exposure of hospital personnel to residual radioactive material outside the patient within the deadspace of the cannula or syringe. Although the volume is small, leaving drugs or radioactive material in the deadspace is also wasteful when considered collectively throughout the year in a large hospital.

The present invention functions to specifically allow the aspiration of a capacitance storage volume of a flush volume, which can later be used to flush the deadspace of the reservoir and the deadspace of a tubing system and catheter. This invention is usable in many medical environments, including the administration of drugs wherein deadspace drug must be flushed from the system and the collection of blood wherein the flush solution must be isolated from undiluted blood to provide a pure blood sample or where the deadspace of the syringe must be flushed free of blood for repetitive fixed reuse with indwelling catheters.

The sequential aspiration syringe comprises a variable volume chamber, such as a syringe barrel or cylinder having an opening which can include a conduit adjacent the distal end for flowing liquid into and out of the chamber. The injection system further includes a volume adjuster, such as a piston with a handle for adjusting the volume within the variable volume chamber. The syringe further includes a chamber divider, which can be a second piston that is positioned within the chamber. The volume adjuster is linked to the divider by a connector or tensile element such as a tether. The tensile element is preferably flexible and collapsible, and preferably filamentous. The chamber divider effectively divides the chamber into two variable volume reservoirs, a proximal or upper primary reservoir and a distal or lower secondary reservoir. The syringe further includes a flow channel which may be in a fixed position along the barrel adjacent the distal end or which may be moveable and carried by the divider piston, or which may be dynamically formed by a positionally-derived flow space or separation between the divider piston and at least a portion of barrel wall when the divider piston is positioned adjacent the distal end. The syringe further includes a valve which enables fluid to pass through the flow channel around or through the chamber divider to pass between the secondary reservoir and the primary reservoir. The valve can be the divider piston or can be located within or otherwise carried by the divider piston. The flow channel preferably provides for hi-directional flow between reservoirs. In one preferred embodiment, the passage of fluid through the flow channel can be enabled or disabled by positioning the chamber divider at different positions along the chamber. In one preferred embodiment, flow through the flow channel is disabled by traction on the tensile element and flow is enabled by contact between the divider and the distal end of the barrel. The positionally selective enablement and disablement of the venting of fluid about the chamber divider provides a mechanism for the preset selective adjustment of maximum volume of aspirated fluid within either the secondary reservoir or the primary reservoir, and for the sequential administration of this fluid from the secondary reservoir and the primary reservoir. In the preferred embodiment, the primary reservoir has a fixed maximum volume. The primary and primary reservoirs are in fluid connection with the conduit connected to the distal end of the chamber so that fluid may flow from either reservoir through the conduit and out of the injection system.

The stop for stopping the divider piston face from pressing against the tapered end and thereby trapping fluid between the face and the tapered end can be positioned upon the face of the divider piston, along the bore, or can comprise complimentary detents for engaging the handle or the main piston and thereby preventing further advancing force of the handle and main piston against the divider piston.

The main piston can reduce pressure within the upper primary reservoir, and the tensile element can selectively lower the pressure in the secondary reservoir when the tensile element is extended and the primary reservoir has been filled. The tensile element can provide for equivalent retraction of the main piston and the divider piston when the primary reservoir has been filled to prevent lowering pressure within the primary reservoir even with further retraction on the main piston so that substantial fluid flow into the primary reservoir would be inhibited even without a valve which disables flow between the reservoirs after primary reservoir filling.

In operation, prior to use, both reservoirs are preferably empty. Initially, there is fluid communication between the secondary reservoir and the primary reservoir. The divider is preferably positioned so that the secondary reservoir has very little or no internal volume. In operation, the distal conduit is connected to a source of fluid such as a blood line or the distal conduit is connected to a cannula which is inserted into a saline flush vial or the like. The volume of the primary reservoir is then increased by the volume adjuster to cause flow of fluid into the distal conduit and then through the flow channel and into the primary reservoir. The flow through the flow channel is preferably enable by positioning the divider adjacent the distal end, which is the resting position of the divider prior to use. During this time, the divider is preferably restrained from moving, as by a detent, thereby preventing enlargement of the secondary reservoir and assuring the divider remains in the venting position despite the relative negative pressure within the primary reservoir. This also allows the nurse to freely turn the syringe upward to expel any aspirated air without effecting the contents of the secondary reservoir. When the primary reservoir is fried (usually with saline), the tensile element connecting the volume adjuster and the chamber divider becomes fully extended and pulls the chamber divider against the restraining detent. This provides tactile indication of completed filling of the primary reservoir, although other indicating means would also be effective. The nurse then can connect to a distal conduit to a second liquid source such as a drug vial. Further retraction then causes the divider to displace from the venting position. The tensile element is preferably strong, but of minimum fluid displacement volume, such as a nylon filament. Upon displacement, the flow channel is closed so that additional fluid does not pass into the primary reservoir. The volume of the secondary reservoir is then enlarged so that fluid passes through the distal conduit into the secondary reservoir until the secondary reservoir is adequately filled. Again, the nurse can turn the syringe upward after aspiration and expel any aspirated air from the secondary reservoir without effecting the contents of the primary reservoir. At this time, the flow channel which previously provided fluid communication between the primary reservoir and the distal conduit is closed so that fluid cannot flow from the distal conduit into the primary reservoir. Furthermore, the secondary reservoir is isolated from the primary reservoir so that mixing of the fluids between the reservoirs cannot occur. Once both reservoirs have been adequately filled the container now includes two sequentially stored volumes of fluid which are isolated one from another and which may contain distinctly different solutions. When injection is desired, each volume of fluid can now be forced in a sequential fashion back through the distal conduit in the reverse order in which they were stored. To inject the fluid, the volume adjuster is advanced, thereby increasing the pressure within the primary reservoir which is transmitted to the secondary reservoir. When the pressure within the secondary reservoir is increased, fluid can move from the secondary reservoir into the distal conduit. However, during this time, the flow connection between the distal conduit and the primary reservoir is disabled so that flow cannot move from the primary reservoir to the distal conduit even if pressure is increased within the primary reservoir. With advancement of the volume adjuster, the primary reservoir moves along the chamber while maintaining a constant volume, the hydraulic force of the trapped liquid causing the divider to advance. Once the secondary reservoir has emptied, the flow between the primary reservoir and the distal conduit is enabled. The enablement is preferably induced when the divider enters the venting region adjacent the distal end of the chamber and may be activated by contact with the distal end of the chamber. Means to indicate enablement of vented flow can be included such as a marker located at a position of the handle or a detent. When the divider is in this position, flow can occur between the primary reservoir and the distal conduit. During this time, as the primary reservoir empties, the tensile element collapses, coils, or folds such that the movement of the volume adjuster toward the divider is preferably not inhibited. In this way, it can be seen that at least two different fluids may be sequentially withdrawn into and stored within the chamber and isolated one from the other by first withdrawing fluid in the primary reservoir and then withdrawing a different fluid into the secondary reservoir. These fluids may then be injected sequentially in the reverse order of aspiration, first from the secondary reservoir and then from the primary reservoir. The fluid from the primary reservoir is preferably circumferentially expelled through the deadspace of the secondary reservoir and conduit to allow a complete flush of the system and the volume of the primary reservoir can be preset to assure a complete flush of the secondary reservoir and conduit. Also, this sequential aspiration and injection preferably occurs through the same distal conduit so that there is no need to disconnect and reconnect for sequential aspiration and/or injection of fluids. It can be seen that when the flow channel is not in fluid connection with the primary reservoir that the primary reservoir and the two pistons represent a single retractable piston assembly with a proximal and distal portion separated by the primary reservoir and with a fixed internal volume and with a fixed piston assembly length, as defined by the tether element. The piston assembly can move along the barrel and the piston assembly can collapse to shorten in length when the fluid escapes from the primary reservoir and can enlarge in length when fluid enters the primary reservoir, both shortening and lengthening occurring to movement of the proximal portion toward or away from the distal portion.

An example of use is with blood sampling, wherein fluid without blood admixture can be stored in the primary reservoir and blood and fluid mixture can be stored in the secondary reservoir. Alternatively, for the administration of drug solutions, it can be seen that saline can be initially drawn into the primary reservoir and the drug solution drawn into the secondary reservoir. When the distal end of the distal conduit is then connected to an intravenous line of a patient, the reservoirs are emptied in the reverse order in which they were filled such that the drug solution is injected into the patient followed by the injection of saline. All of this can be achieved with much greater simplicity since disconnection and reconnection of multiple syringes are no longer necessary when utilizing this device.

In another system embodiment for blood sampling, the syringe can be permanently attached a second conduit which is connected to a first conduit with an access port intermediate the first and second conduit. The fast conduit is connected to a terminal of a conventional catheter, for example, a multilumen catheter. (These catheters often have a low internal fluid volume so that very little resident flush solution is available within the catheter for filling the primary reservoir.) The first conduit of the system includes an access port which can be utilized for drawing a blood specimen or for infusing liquid. Indeed, an intravenous tubing could be connected to this access port so that liquid can continuously infuse through this port when a blood sample is not being obtained. The maximum displacement volume of the primary reservoir can be preset so that it is less than the internal fluid volume of the first conduit, the second conduit, and the internal fluid volume of the catheter. In this way, this volume can be preset so that, upon withdrawal of fluid into the syringe, only flush solution will enter the primary reservoir. The syringe can, therefore, can be used to draw fresh pure blood past the access port for sampling by insertion of a cannula through the access port. It is considered preferable to have a minimal deadspace intermediate the syringe and the access port so as to provide adequate saline flush of all residual blood from the deadspace with minimal flush volume. The system can be constructed such that substantial priming deadspace of resident flush solution is supplied with the first conduit intermediate the access port and the blood vessel. This assures that adequate flush volume is present so that the primary reservoir can aspirate a large enough flush volume to later provide an adequate flush of the primary conduit and the deadspace intermediate the syringe and the access port. In another embodiment, the access port is positioned adjacent the distal end of the syringe so that substantially no deadspace is present between the distal end of the syringe and the access port, thereby further minimizing the requirement for higher flush volumes. Whether the access port is placed without deadspace in juxtaposition with the syringe or whether the access port is connected by a low deadspace conduit will depend upon whether it is desirable to place the syringe directly upon the catheter or at some distance from it. In any case, the volume of the secondary conduit is preset during manufacture to be less than the internal fluid volume of the catheter and the conduit portions distal the syringe. Subsequent each blood aspiration maneuver, some blood mixed with fluid will remain within the first conduit or catheter and this can be easily flushed by inserting a cannula into the access means and flushing saline through the access means. Also, with this system, any source of fluid which is connected to the second conduit or otherwise proximal the access means could effectively flush any residual blood distal the access means after each blood withdrawal maneuver.

It is, therefore, the purpose of this invention to provide an apparatus and method that will eliminate the need for multiple syringes for the administration of drugs through IV systems. It is further the purpose of this invention to provide a simplified method and apparatus for the sampling of blood from an indwelling catheter within a patient's blood vessel which does not require the use of a first syringe to withdraw and discard the resident portion of fluid within the catheter and associated tubing system. It is further the purpose of this invention to provide a system for withdrawing blood into a syringe and flushing the blood back out of a syringe utilizing reciprocating saline volumes with minimal additional volume administration to the patient and further simplifying the process of syringe flushing, as for repetitive undiluted blood isolation within arterial lines for sampling or ex vivo testing. It is further the purpose of this invention to provide an inexpensive device which allows blood collection and drug administration with a single unified apparatus, thereby reducing overall cost of manufacture. It is further the purpose of this invention to provide an inexpensive blood collection and drug administration system which utilizes a novel, simple method of sequential Withdrawal of liquid followed by sequential injection in the reverse order of the withdrawal, which method simulates conventional single syringe aspiration and injection, thereby providing greater ease of use for nursing personnel. It is further the purpose of this invention to provide an apparatus having an inexpensive means, such as a filamentous tensile element, for adjusting the maximum volume within the primary reservoir during manufacture so that a wide range of such devices having different maximum volumes can be manufactured for different applications without substantial increase in manufacturing cost. It is further the purpose of this invention to provide a single unified apparatus and method for the compartmentalization and isolation of two different fluids within a single syringe utilizing a single withdrawal maneuver and to allow the nurse to expel aspirated air from either compartment during each withdrawal process and to provide the subsequent sequential injection of these two different fluids utilizing a single injection maneuver. It is further the purpose of this invention to provide a multiple reservoir syringe which includes a bi-directional, positionally-enabled, circumferentially-directed flushing and aspirating mechanism which freely vents a high flow of fluid from a primary reservoir upon completed injection of liquid from a secondary reservoir to completely flush the secondary reservoir free of blood or drug solution with a minimum volume of fluid. It is further the purpose of this invention to provide and inexpensive system for connecting, within a syringe sequential pistons with a tensile element of low fluid displacement volume and high flexibility to allow delayed distal piston retraction at a predetermined volume during proximal piston withdrawal and subsequent uninhibited proximal piston advancement toward the distal piston to achieve a simplified method of sequential aspiration and flushing and so that the internal volume of the syringe is not significantly effected by the displacement volume of the element. It is further the purpose of the invention to provide a mechanism for disabling flow between a proximal and a distal reservoir which is activated at a specific filling volume of the primary reservoir and which is activated by retraction of a tensile element. It is further the purpose of this invention to provide an automatic flushing syringe which can be used with automatic, electronic, or mechanical injection systems for unattended injection and subsequent flush into a patient with a single syringe. These and other objects and advantages of the invention will be further set forth in the description which follows and, in part, will be learned from the description or may be learned by practice of the invention. The objects and advantages of the invention may be realized by means of the instrumentalities and combinations particularly pointed out in the appended claims.

BRIEF DESCRIPTION OF THE DRAWINGS

FIG. 6a is a schematic illustration of a syringe in accordance with the present invention in operation for blood sampling;

FIG. 6b is a view similar to FIG. 6a showing the syringe plunger being retracted;

FIG. 6c shows the filled syringe allowing for blood transfer to a container;

FIG. 7 show the syringe of the invention following blood transfer to the container;

FIG. 8 is a schematic illustration of a syringe in accordance with the invention incorporated into a blood aspiration assembly;

FIG. 8a is an enlargement of an area of FIG. 8;

FIG. 9 shows the blood aspiration assembly of FIG. 8 in blood sampling mode;

FIG. 9a is an enlargement of an area of FIG. 9;

FIG. 12 shows the partially filled syringe being aligned with a drug vial;

FIG. 13 is a view similar to FIG. 12 showing the plunger further retracted to load a drug;

DESCRIPTION OF THE PRESENTLY PREFERRED EMBODIMENTS

Figures 1, 3:
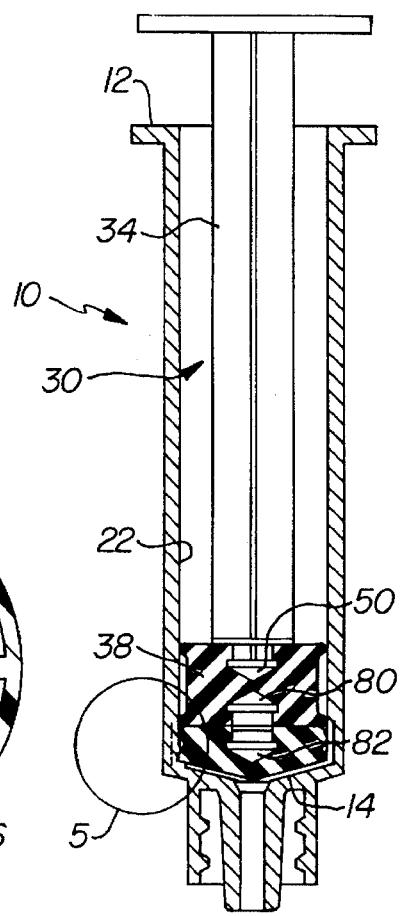
FIG. 1 is a schematic elevational view partly in cross-section of a sequential compartmentalized fluid aspiration and injection syringe in accordance with the present invention.
FIG. 3 is a schematic cross-sectional view taken along line 3—3 of FIG. 2.
Figure 4:
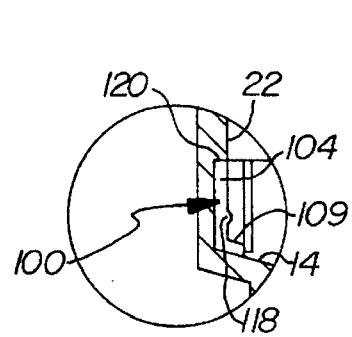
FIG. 4 is a detail of area 4 in FIG. 2.
Figure 5:
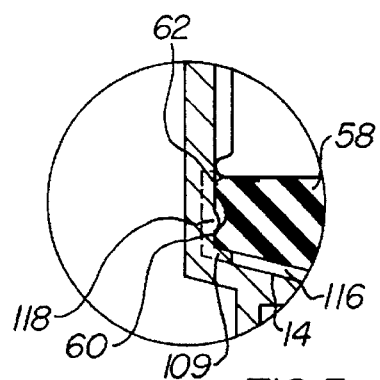
FIG. 5 is a detail of area 5 in FIG. 1.
Figure 10:
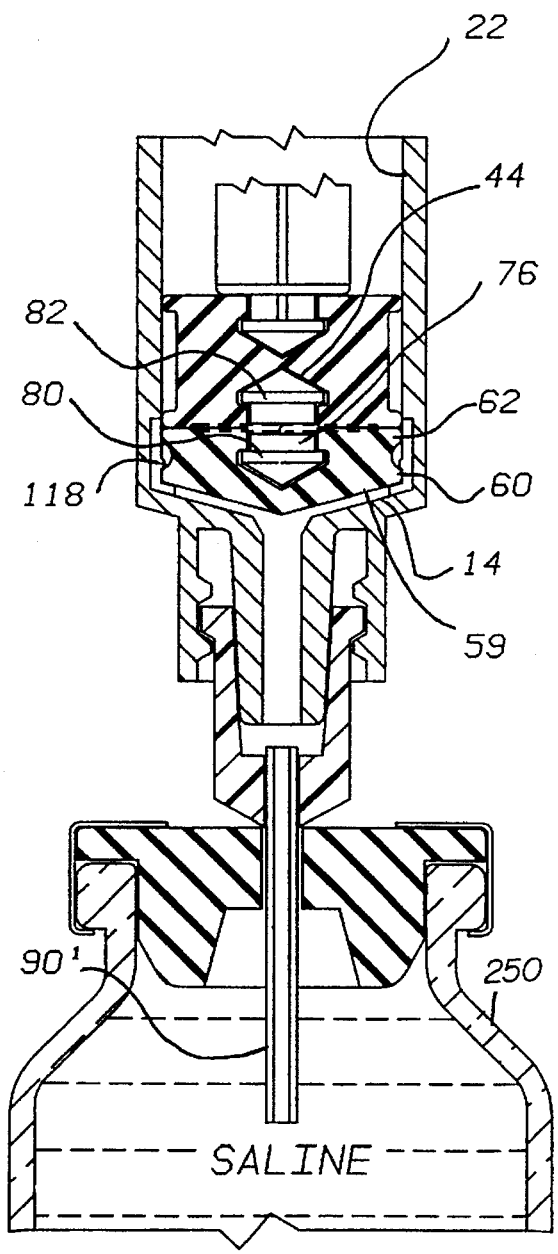
FIG. 10 is an enlarged elevational view of a syringe in accordance with the invention for use in drug solution administration.
Figure 11:
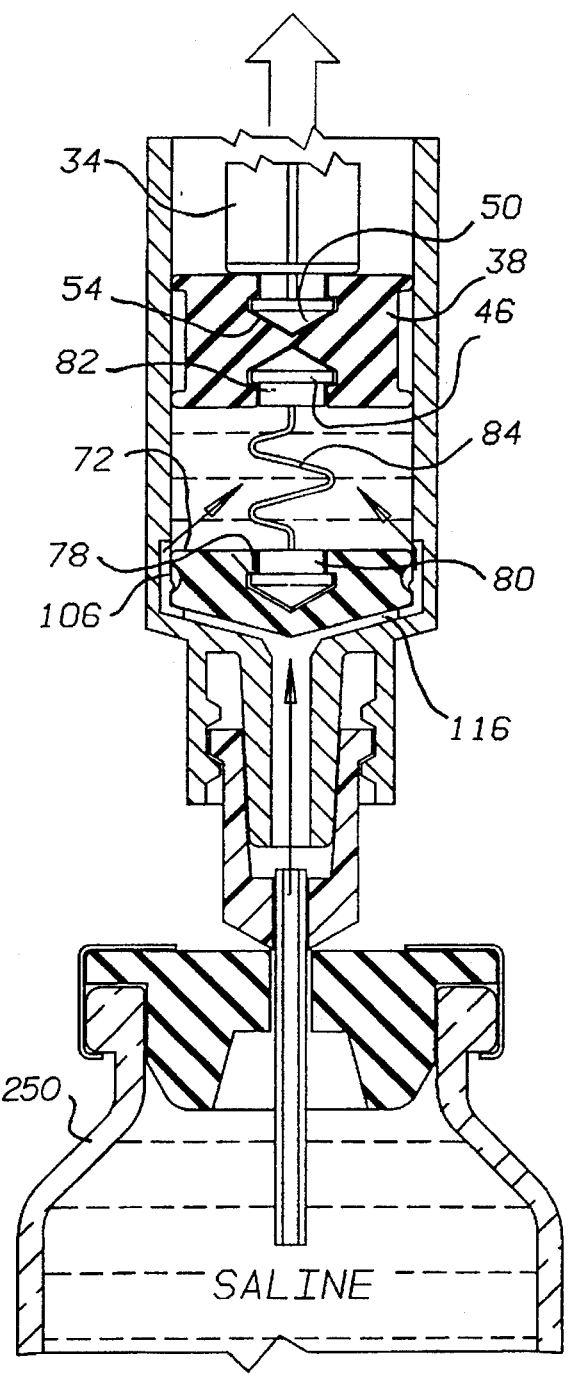
FIG. 11 is a view similar to FIG. 10 showing the syringe plunger being retracted.

The sequential compartmentalized fluid aspiration and injection syringe 5 (FIG. 1) includes a syringe barrel 10 having a proximal base 12 and a distal tapered portion 14 extending to distal tip 18. The syringe barrel includes a main bore 22 which is in fluid connection with distal conduit 26 extending through the distal tip 18. The apparatus includes a main piston 38 having a handle 34 including inner face 39 and wipers 40 and 42. Piston 38 is preferably comprised of lubricated robber. The innerface 39 includes a recess 44 with a retaining lip 46. The handle 34 includes distal tip portion 50 which can be forced through the recess 54 in the piston 38. After insertion through the recess 54, the handle tip 50 is retained within the piston 38. The apparatus further includes an cylinder divider piston 58 which preferably appears relatively similar to the main piston 38 and can be similarly fashioned. Divider piston 58 is likewise preferably comprised of lubricated rubber having lateral sealing potions as distal wiper 60 and as proximal wiper 62. The divider piston 58 has a lower face 59 that is preferably sloped to conform with the tapered distal end 14. The divider piston 58 further includes an upper face 72 with a recess 76 having lip 78 for receiving a tether retainer 80, as will be described. A connecting tensile element or tether 84 is provided, which is preferably filamentous and of low fluid displacement volume, having a proximal tether retainer 82 and a distal tether retainer 80 for respective insertion and retention within the piston 38 and the cylinder divider piston 58, respectively. The tether 84 is preferably comprised of a flexible material such as polyethylene or nylon filament and may be integral with or otherwise attached to the tether retainers 80 and 82. The tether 84 preferably should have substantial tensile strength and preferably should be able to withstand a 10–15 pound longitudinal pull force without breaking. The diameter and shape of the bore 22 of the syringe barrel 10 and the diameter and shape of the piston 38 and cylinder divider piston 58 are all matched so that the piston 38 and the cylinder divider piston 58 seal tightly within the main bore 22 of the syringe barrel 10. The bore 22 diameter is uniform along the main portion 85 of the barrel 10 to provide uniform seating and sealing of the main piston 38 and cylinder divider piston 58. A vent portion 100 is provided adjacent the tapered portion 14 of the syringe barrel 10. In the preferred embodiment, the vent portion 100 includes multiple flow channel slots 104 having an axial length which is greater than the length of the cylinder divider piston 58. The slots 104 are separated by radially projecting linear ribs 106, each having a smooth innersurface 108. The diameter of the syringe bore 22 when measured transversely from the innersurfaces 108 of opposing ribs is equivalent to the diameter of the syringe bore 22 throughout the length of the barrel main portion 85 so that the cylinder divider piston 58 is seated against the innersurfaces 108 of radially projecting ribs 106 when the cylinder divider piston 58 is positioned within the venting portion 100, as shown in FIG. 1 and FIG. 11. This allows free reciprocating movement over the slots 106 with maintenance of stability of the divider piston 58. Several seats 109 are provided which prevent contact of the lower face 59 against the taper portion 14, thereby forming, upon complete advancement of the divider 58, a circumferential flush flow space 116. The seats or stops 109 preferably inhibit advancement of the lower face 59 beyond a distance of 2 mm from the tapered portion; although, up to 5 mm is acceptable when larger flush volumes are being used. The small size of the flush space 116 allows complete flushing with minimum flush volume. Several of the ribs 106 can include radially projecting detents 118 to retain the cylinder divider piston 58 in the venting position by engaging the distal wiper 60, as shown in FIG. 5. Other means for retention may be used. For example, the transverse diameter of the syringe bore 22 may be slightly reduced (not shown) at the level of the ribs 106 so as to provide slight compression of the cylinder divider piston 58 to reversibly retain the cylinder divider piston 58 within the vent portion 100.

Figure 2:
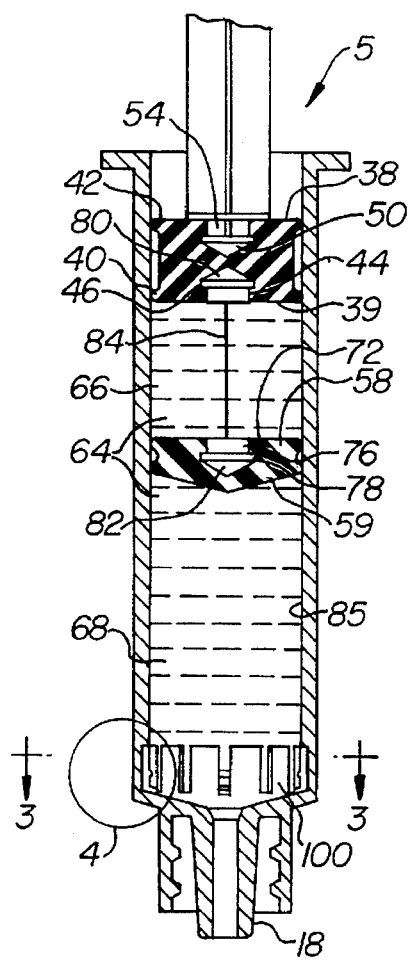
FIG. 2 is a view similar to FIG. 1 showing the piston in the retracted position.

In assembly, the tether retainers 80 and 82 are inserted into their respective recesses 76 and 44 of the cylinder divider piston 58 and piston 38. The reservoir divider piston 58 and the piston 38, with its attached handle 34, are inserted into the syringe barrel 10. When so assembled, syringe 5 defines a chamber 64 (FIG. 2) which is divided by the cylinder divider piston 58 into two separate variable volume reservoirs, a primary reservoir 66 and a secondary reservoir 68. The handle 34 is then fully advanced so that the innerface 39 of piston 38 forces the cylinder divider piston 58 into the venting position adjacent vent portion 100 past detent 118 against the seats 109 with the cylinder divider piston 58 (as in FIG. 1) contacting the ribs 106 and the piston 38 being adjacent the cylinder divider piston 58 and the circumferential flow space 116 between face 68 and tapered portion 14, (as is shown in FIG. 1 and FIG. 5).

The method of operation depends upon the environment in which the invention is being used. One of the primary advantages of the present invention is the fact that this syringe can be utilized for several different operations which previously involved either the use of sequential aspiration utilizing two separate syringes (as during intermittent blood sampling) or sequential injection utilizing two separate syringes (as in IV drug administration) or both sequential aspiration and sequential injection (as in repetitive blood isolation for testing or sampling from arterial lines.) The utilization of a single apparatus which can accomplish many widely-used tasks within the hospital provides additional value in that familiarity with the device is increased and the cost can be reduced by increased utilization throughout many different hospital areas.

In operation for blood sampling, the syringe 5 can be used in several different ways. For example, when repetitive blood sampling is not required, the nurse can utilize the device as a single disposable unit to collect and transfer a single blood specimen. This transfer operation is illustrated in FIGS. 6 and 7. A needle or cannula 111 is attached to the distal tip 18. A protected needle or cannula, such as described in my U.S. Patent application Ser. No. 08/043,636 (the disclosure of which is hereby incorporated by reference as if completely disclosed herein) may be used. The cannula 111 is inserted through the septum 118 of a terminal 113 of a catheter 114 within the blood vessel 115 of a patient. The handle 34 is retracted and the initial fluid contained within the terminal 113 and the catheter 114 is drawn into the distal conduit 26 of the syringe 5 and flows through the flow channel slots 104 of the vent portion 100 around the cylinder divider piston 58 into the secondary reservoir 68. The primary reservoir 66 is filled until the tether 84 becomes fully extended. During this time, the divider is retained by detents 118 so that the secondary reservoir 68 does not enlarge. In addition, since the tether 84 is not extended, there is no pull against the divider piston 58. The slots 104 and circumferential flow space 116 preferably have cross-sectional areas at least equal to that of the distal conduit 26 so that fluid can rapidly flow around the divider piston 58 to reduce the potential for a relative vacuum to develop in the secondary reservoir 68 which could displace the divider 58 out of the venting position. Once the tether 84 is fully extended, the primary reservoir 66 is filled. At this time, further retraction upon the syringe handle 34 causes the extended tether 84 to retract divider piston 58 out of the venting position, overcoming detent 118 and resulting in displacement of the cylinder divider piston 58 proximally, as in FIG. 2. Generally, a slight increase in force is required to displace the cylinder divider piston 58 from the fully advanced position by overcoming the detents 118. This slight increase in resistance provides a useful indication for the nurse that the syringe 5 is now withdrawing pure blood into the secondary reservoir 68, as will be discussed. A mark 130 (FIG. 7) can also be provided on the handle 34 for this purpose. As noted, continued withdrawal of the handle 34 after the tether 84 has reached its maximum length will cause the tether 84 to pull the cylinder divider piston 58 from its vented position and this will bring the proximal wiper 62 into complete sealing contact with the smooth circumferentially continuous bore 22 of the barrel 10. Immediately upon movement of the cylinder divider piston 58 to the end 120 of the vent portion 100, the slots 104 of vent portion 100 are thereby sealed closed to the primary reservoir 66 by the proximal wiper 62 so that no further fluid may move through the slot 104 into the primary reservoir 66. The primary reservoir 66 is therefore completely isolated from the secondary reservoir 68 by the tight seal provided by the wiper 62 and wiper 60 against the smooth continuous bore 22. This fixes the volume within the primary reservoir 66 and this volume is therefore a function of the length of the fully extended tether 84 and the diameter of the bore 22. Further withdrawal of the handle 34 will came the piston 38 to cause further retraction upon the cylinder divider piston 58, thereby pulling the cylinder divider piston 58 further proximally and drawing pure blood into the secondary reservoir 68. Actually, once the wiper 62 has established a complete circumferential seal, the tether is no longer necessary for retraction since the divider 58 will retract with the piston 38 to accommodate the negative pressure produced by withdraw of the piston 38. The tether 84, therefore, functions as a valve activator and volume adjuster by setting the volume of the primary reservoir 66 at which volume tho primary reservoir 66 will be filled and sealed. A pure undiluted blood sample is assured by setting the length of the tether 84 in assembly to provide an adequate volume to remove all resident fluid from the catheter 114 and terminal 113. Generally, a primary reservoir 66 volume of 5 cc is adequate to assure that all resident fluid has been removed from most conventional catheters and terminals, such as multilumen central venous catheters. Once the pure blood sample has been withdrawn into the secondary reservoir 68, the cannula 111 can be removed from the terminal of the multilumen catheter and then inserted into, for example, an evacuated container 140, as shown in FIG. 6c. A blood transfer apparatus such as that shown in my U.S. Pat. No. 5,114,400 (the disclosure of which is hereby incorporated by reference as if completely disclosed herein) may be used and, at this point, pure blood can be transferred from the secondary reservoir 68 into the evacuated container 140.

In this way, it can be seen that the syringe 5 accomplishes automatic separation of the "discard volume" of resident fluid (which will be mixed with some blood) in the primary reservoir 66 from the undiluted blood sample in the secondary reservoir 68. A volume of 5 cc of the primary reservoir is generally suitable to provide an adequate "discard volume" when the device is used for most conventional central venous catheters. The separated pure blood sample within the secondary reservoir 68 can then easily then be transferred into an evacuated container for transport to the laboratory.

The sequential compartmentalized fluid withdrawal and injection syringe 5 can also be incorporated into a blood aspiration assembly, as disclosed in my U.S. Pat. No. 4,838,855 (the disclosure of which is hereby incorporated by reference as if completely disclosed herein). The blood aspiration system 200, shown generally in FIGS. 8–9, includes a first conduit 204 which is connectable to a catheter 208 for insertion into a blood vessel 209. The first conduit 204 engages an ex vivo measurement apparatus sensing unit for measurement of the partial pressure of oxygen, carbon dioxide, and other parameters, as are known in the art. Additionally provided along the first conduit 204 is a blood aspirator receiver 210 which can include a resealable septum 211 which can be of the type as described in my U.S. Pat. No. 5,178,607 (the disclosure of which is hereby is incorporated by reference as if completely disclosed herein). The system further includes a second conduit 212 which is connected to a valve 214, such as a conventional stop-cock. A third conduit 218 can be provided which is connected to a high pressure fluid source (for example, a bag of pressurized saline solution). In addition, a pressure transducer may be provided and is preferably positioned along the third conduit 218. A one-way flush valve 230, as is known in the art, is further provided intermediate the high pressure source and a syringe 5'. The syringe 5' is of the design as discussed supra and is provided with barrel 10' and bore 22' and including the piston handle 34' and piston 38' which is connected by a tether 84' (FIG. 9a) to a cylinder divider piston 58', defining a primary reservoir 66' and a secondary reservoir 68'.

In operation, the system 200 is normally filled with resident fluid, such as heparin solution or saline, and connected to catheter 208 which has been inserted into the blood vessel 209 of a patient. During this time, the valve 214 is closed to the syringe 5' and opened to provide fluid communication between the high pressure source and the blood vessel 209. Furthermore, during this time, the pressure within the blood vessel 209 can be monitored by the pressure transducer. When a blood sample is desired, the valve 214 is positioned so that fluid communication is opened between the syringe 5' and the blood vessel 209 and closed to the high pressure source. At this time, both the piston 38' and the cylinder divider piston 58' are in the fully advanced position and the cylinder divider piston 58' is in the vented position against the fibs 106' (as shown in FIG. 8a). When a blood sample is required, the nurse withdraws the handle 34' which retracts the piston 38', withdrawing the resident heparin solution from the second conduit 212 through the slots 104' and into the primary reservoir 66'. The maximum volume of the primary reservoir 66' is set by the length of the tether 84 and predetermined to be less than the combined internal fluid volume of the first and second conduits 204 and 212 so that no blood, or negligible amounts of blood, enters the primary reservoir 66' and so that the primary reservoir 66' is completely filled with the resident flush solution. The operation, advantages, and rationale for this novel reciprocating volume relationship is discussed in detail in my U.S. Pat. No. 4,838,855 and further in the medical journals, *Critical Care Medicine,* vol. 21, no.4, p. 481, April 1993 and Chest, vol. 104, no. 6, p. 1711, December 1993.

With the present invention, a volume of approximately 2 cc is a suitable maximum internal volume for the primary reservoir 66'; although, other volumes may be used. A volume of 3 cc is a suitable combined internal fluid volume of the first and second conduits 204 and 212 for use (for example) with conventional radial arterial catheters, although other volumes may be used. Once the primary reservoir 66' is completely filled and the tether 84' is fully extended, further retraction on the handle 34' will withdraw the cylinder divider piston 58' upward and away from the vented position. As discussed previously, when the cylinder divider piston 58' moves away from the vented position, the divider wipers 62 contact the bore 22' tightly to provide a complete circumferential seal against the smooth bore 22' such that no further fluid can move from the distal conduit 26' to the primary reservoir 66'. As the piston is further retracted (FIG. 9a), fluid moves into the secondary reservoir 68'. The secondary reservoir 68' is then filled with a mixture of blood and heparin solution with adequate volume to cause substantially undiluted blood to fill the first conduit 204 in response to the pressure gradient caused by the withdraw of fluid into the secondary reservoir 68'. A volume of 3 cc of the primary reservoir 66' is a suitable volume; although, other volumes may be used. At this point, the valve 214 can be closed so that no communication occurs between either the patient and the distal conduit 18 of the syringe 5' or the patient and the high pressure source; and at this time, an aspirator, such as a blunt cannula having an indicator system to prevent pressure-induced blood spurting, as discussed in my U.S. Pat. No. 5,114,400 (the disclose of which is hereby is incorporated by reference as if completely disclosed herein) may be inserted into septum 211 to obtain an undiluted blood sample. Alternatively, measurements may be made by an ex vivo system on the undiluted blood within the first conduit 204. Once the measurements have been made or the blood sample has been obtained, the nurse turns the valve 214 to its position opening fluid communication between the primary reservoir 66' and the patient and at this time the nurse advances the piston handle 34'. As the piston 38' advances, hydraulic force within the primary reservoir 66' causes the cylinder divider piston 58' to advance, thereby causing the blood in the secondary reservoir 68' to empty into the second conduit 212. After the divider 58' has fully advance, any residual blood in the secondary reservoir 68' is flushed out by the circumferential flow of flush solution through slots 104' and out the flush flow space 116'. This clears the syringe 5' of substantially all blood. Any residual blood in conduits 204 and 212 and catheter 208 can be flushed back into the blood vessel 209 using the flush valve 230 after the valve 214 is then again closed to the syringe 5'. The process is now complete. This cycle may be repeated at any time an undiluted blood sample or ex vivo testing is desired.

The invention can also be utilized for the sequential administration of medication and saline flush solution. The embodiment for medication administration can be identical to that utilized for single use blood withdrawal and which is incorporated as syringe 5 in the previously-described blood aspiration assembly. The method of use of the syringe 5 for drug solution administration is shown in FIGS. 10–13. In operation for drug administration, the canula 111' is first inserted into a vial 250 containing saline solution and the main piston 38 is withdrawn by withdrawal of handle 34 until the primary reservoir 66 is filled with saline. At this point, the nurse will feel a resistance to further withdrawal of the piston 38 which is induced by the detents 118 engaging the wiper 60 transmitted through the now fully extended tether 84. Also, a mark can be provided (as will be discussed with another embodiment) to indicate complete filling of the primary reservoir 66. The nurse then withdraws the cannula from the saline vial 250 and inserts the cannula 111 into the drug vial 260 (FIG. 12). The nurse then withdraws the handle 34 so that the cylinder divider piston 58 is pulled by the tether 84 past the detents 118 and the primary reservoir 66 fills with drug solution (FIG. 13). Once the secondary reservoir 68 has been filled with adequate volume of drug solution, the nurse takes the rifled syringe 5 to the bedside and inserts the cannula 111' through the septum of a catheter or intravenous tubing system (not shown) in fluid communication with the patient. The nurse then advances the piston 38 and the secondary reservoir 68 empties of drug solution into the intravenous tubing through hydraulic force within the primary reservoir 66, as previously noted. When the injection of the fluid within the secondary reservoir 68 is complete, the divider piston 58 has reached the venting position and engages the seats 109. At this point, further advancement of the piston 38 causes the saline solution in the primary reservoir 66 to flow through the slots 104 and through the flush flow space 116 to flush around the lower face 59 of the divider piston 58 and out the distal conduit 18 and to flush the deadspace of the intravenous tubing and catheter with saline. The nurse withdraws the cannula while continuing to apply pressure on the piston 38 during the flush maneuver to assure a positive pressure remains within the deadspace of the tubing of the catheter upon the withdraw of the cannula 111. The injection of the drug is now complete and the catheter and tubing system has been flushed and residual positive pressure remains within the catheter and tubing system, thereby achieving a comprehensive sequential injection of drug and saline flush with only a single injection system and without the need for multiple cannulas and multiples insertions. The syringe 5' may also be incorporated into conventional automatic mechanical or electronic injection systems to allow automatic flushing after injection with a single syringe. The algorithms for these mechanical or electronic injection systems can be adjusted to automatically accommodate the flush volume of the primary reservoir so that the nurse need only identify the intended drug injection volume.

Figure 14:
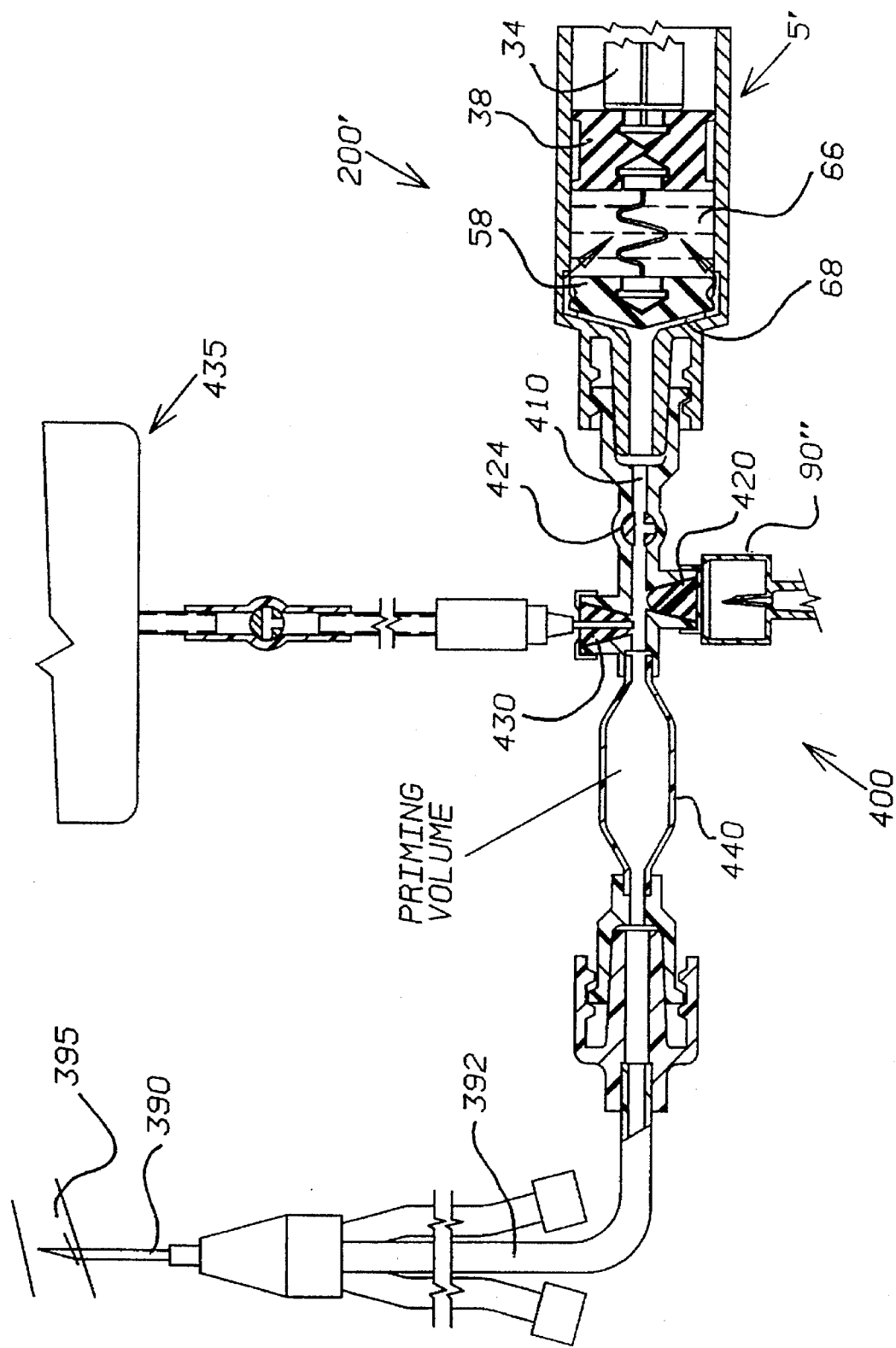
FIG. 14 is a schematic illustration of a syringe in accordance with the invention incorporated into a blood aspiration assembly.

FIG. 14 illustrates another Blood Aspiration Assembly embodiment 200' with a fixed and preferably permanently attached syringe 5'. This design is intended for use with conventional multilumen catheters 390 or other catheters having terminals 392 which may have low internal fluid volumes (often less than 1 cc) and which have been inserted into a blood vessel 395' of a patient. The syringe 5' is attached to a main conduit 400 having a proximal portion 410, the proximal portion 410 is intermediate a fluid injection site 420 and the syringe 5' and includes a blood sampling site 430 and valve 434. The site 430 is reversibly connected to fluid source 435 which may be a syringe (not shown) or a bag of fluid, as shown. The conduit 400 further includes a distal priming fluid storage portion 440 connected to the terminal 392. The distal portion 440 is constructed to have a greater internal fluid volume than the proximal portion 410. The distal portion 440 functions to provide adequate priming of resident fluid storage distal the syringe 5' so that the primary reservoir 66' will have adequate resident fluid available for initial filling and for subsequent flushing of all blood from the secondary reservoir 68' and the proximal portion 410 after the blood specimen has been obtained. The proximal portion 410 has a low internal fluid volume to allow complete flushing proximal the injection site 430 with a minimal flush volume. The priming volume provided in the distal portion functions to add to the internal fluid volume of the catheter (which may be less than 0.5 cc) to allow adequate fluid for subsequent flushing. The priming volume can be, for example, 1–2 cc, but lesser volumes may be used with a smaller syringe 5'. The volume of the primary reservoir 66' is predetermined to be less than the combined internal fluid volume of the catheter 390, its terminal 392, and the conduit 400 (including the primary volume). In combination, volumes of 2 cc for the first conduit, 0.5 cc for the second conduit, and a primary reservoir volume of 1.5 cc will provide an adequate flush volume to assure that the syringe and second conduit are adequately flushed with each blood aspiration maneuver.

In operation, fluid from the fluid source 435 is disabled and the handle 34 of the syringe is withdrawn. This causes the fluid stored in the distal portion 440 to flow into the primary reservoir 66' (where it will be used later to flush the syringe 5' and adjacent proximal portion 410). Upon further retraction, blood enters the system 200' and fills the secondary reservoir 68'. The valve between the syringe 5' and the sampling site is then closed and a blood sample is obtained, as by cannula 111". The valve 424 is then opened and the handle 34' is advanced, flushing the blood back into the patient, the fluid within the primary reservoir 66' flushing the syringe 5' and proximal portion 410. Fluid flow can then be enabled through the injection site 430 to flush any residual blood in the distal portion 440 or catheter 390 back into the blood vessel 395 of the patient.

Although the previously described preferred embodiment utilizing configuration of slots adjacent the distal end to provide positionally-enabled and disabled flow through the flow channel between the primary and secondary reservoir has the advantage of minimizing the number of moving parts, this embodiment may require more complex molding of the syringe barrel. Syringe barrels with smooth continuous bores throughout are in wide clinical use and, for this reason, the manufacturing cost for such syringe barrels is extremely low. It would, therefore, be advantageous to provide an embodiment which does not require any modification of conventional smooth syringe barrels which are presently in wide use and marketed, for example, by Sherwood Medical Corporation and Becton Dickinson Corporation in many different sizes. Other corporations, likewise, produce such inexpensive syringe barrels. The utilization of conventional syringe barrels can substantially reduce development time and, therefore, provide important value from a competitive perspective and can result in more expeditious widespread availability so that the advantages disclosed herein can be more rapidly realized within healthcare delivery facilities.

Figures 15, 16:
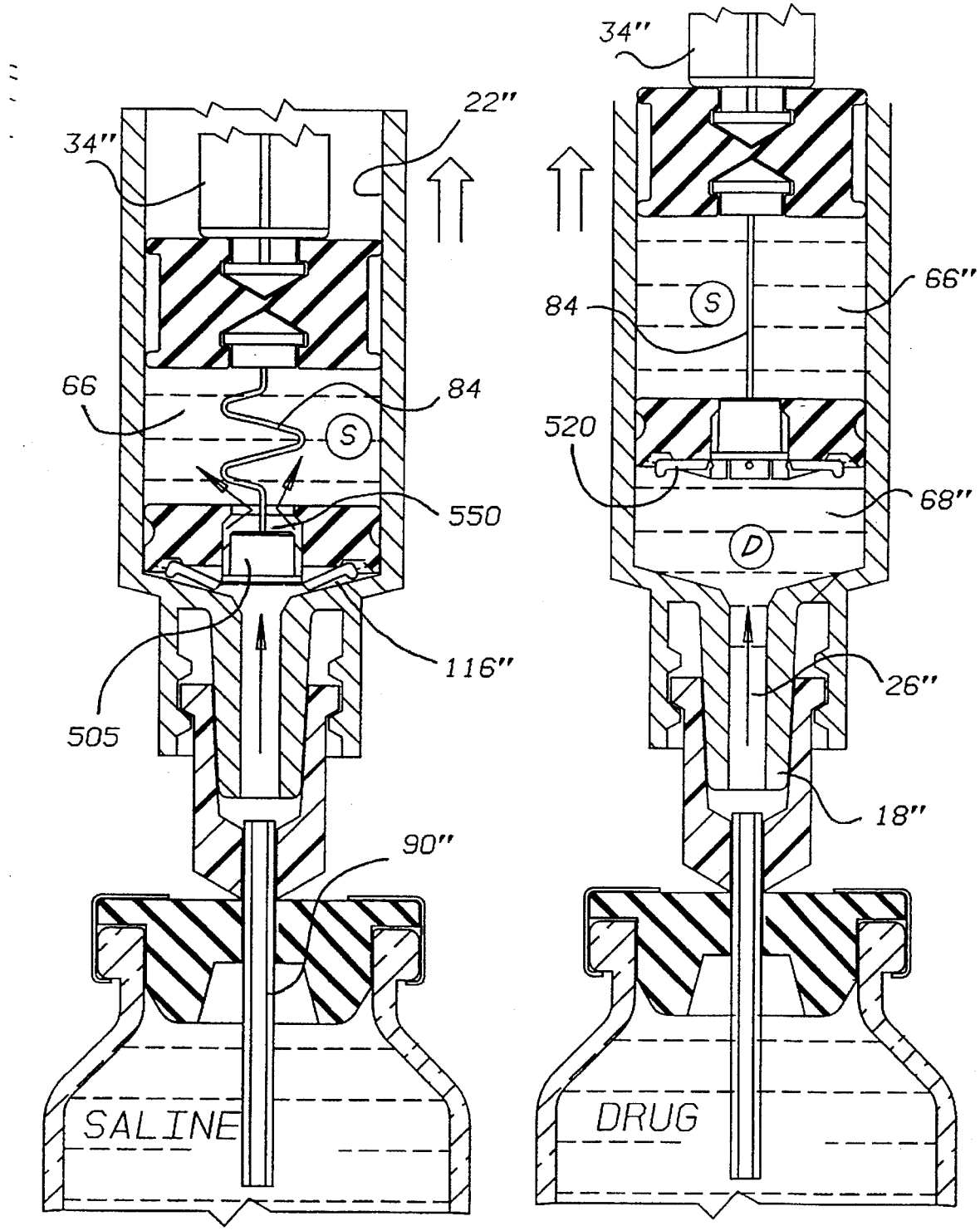
FIG. 15 is an elevational view of a presently preferred embodiment for utilizing conventional syringe barrels and in which the piston is being retracted to load saline.
FIG. 16 is a view similar to FIG. 15 showing further retraction of the piston to load a drug.
Figure 17:
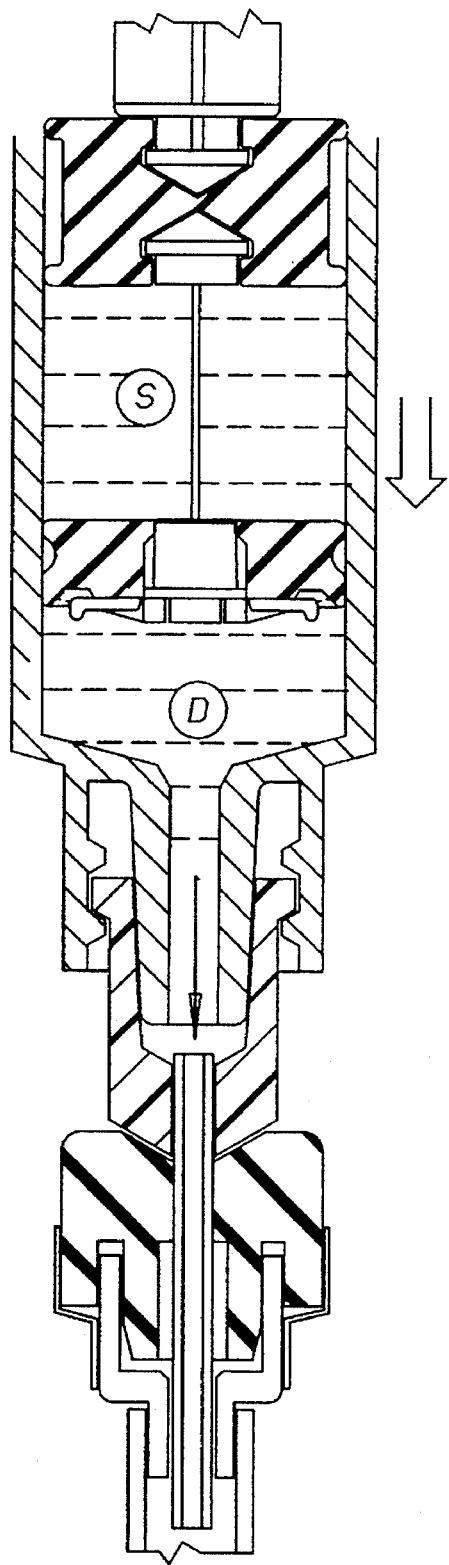
FIG. 17 is a view of the syringe of FIG. 16 in which the piston is being advanced to administer the drug to a patient.
Figure 18:
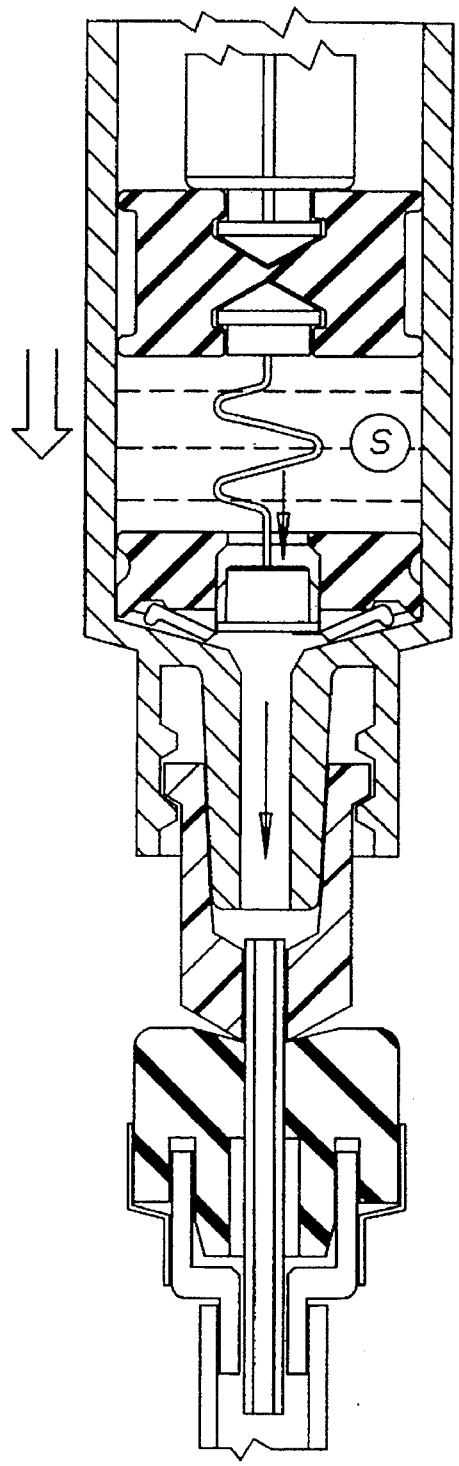
FIG. 18 is a view similar to FIG. 17 showing the administration of saline following administration of the drug.
Figure 19:
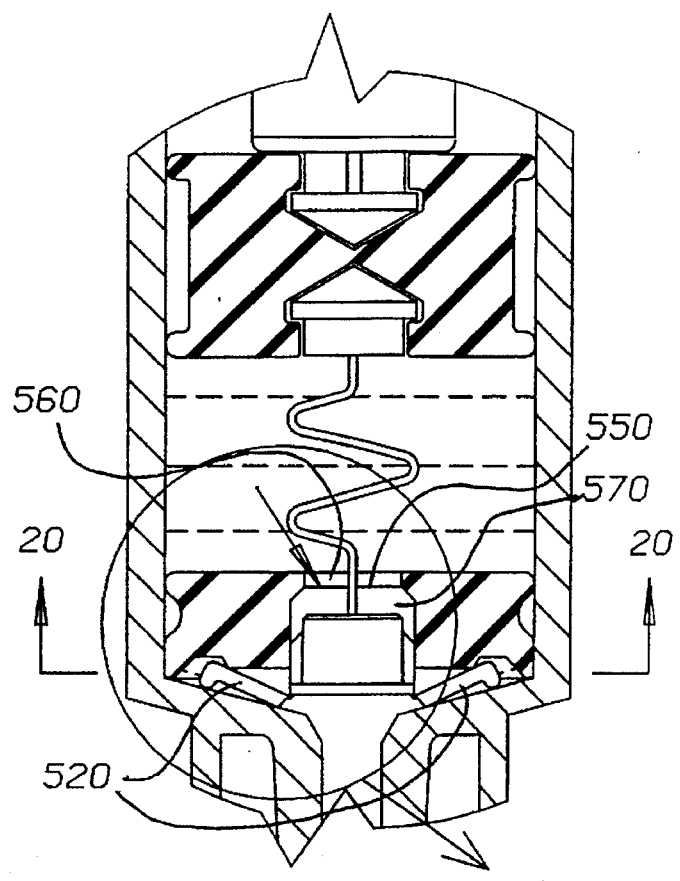
FIG. 19 is an enlarged view of the piston structure shown in FIG. 18.
Figure 19A:
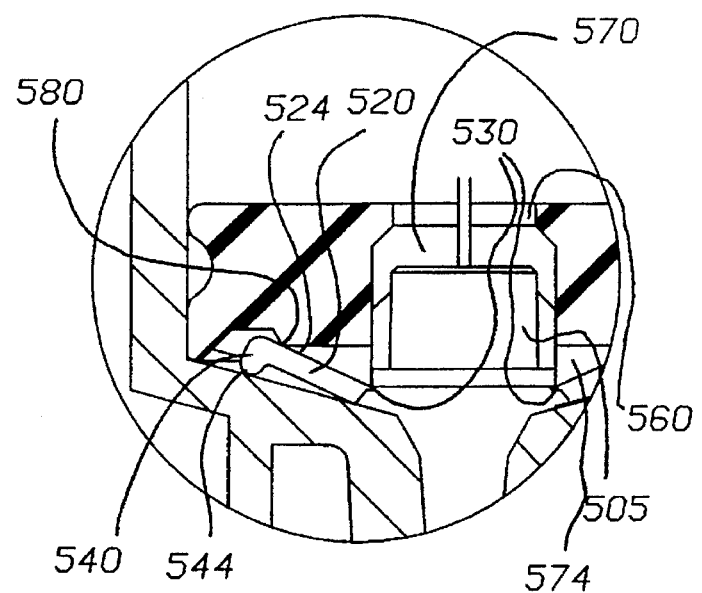
FIG. 19a is an enlargement of area 19a of FIG. 19.
Figure 21:
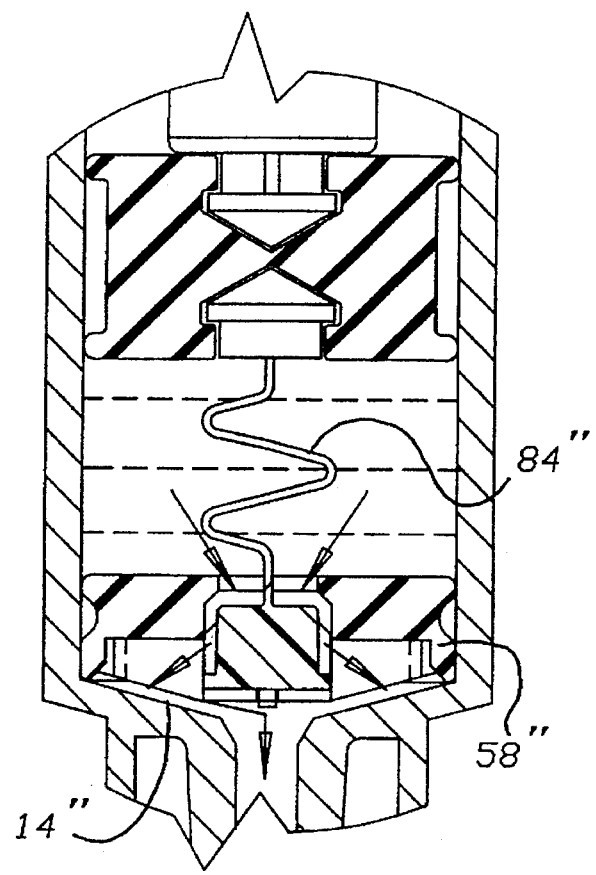
FIG. 21 is a view taken in the direction of line 21—21 showing fluid flow in the syringe of FIG. 19.
Figure 20:
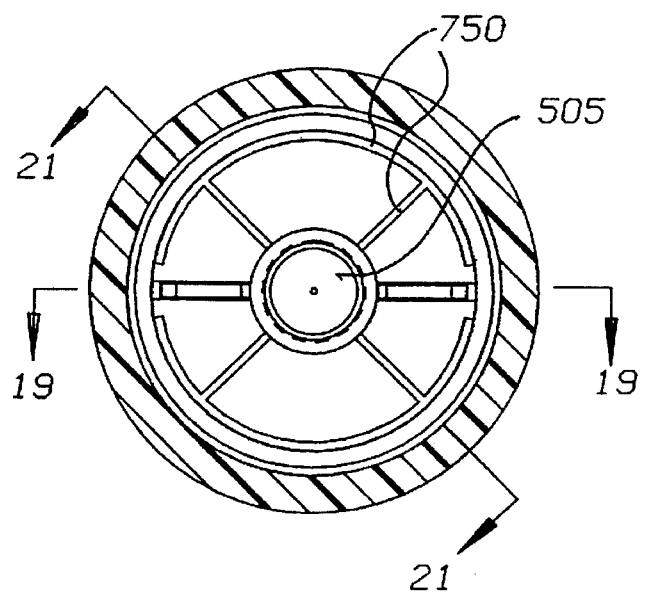
FIG. 20 is a view taken along line 20—20 of FIG. 19.
Figure 22:
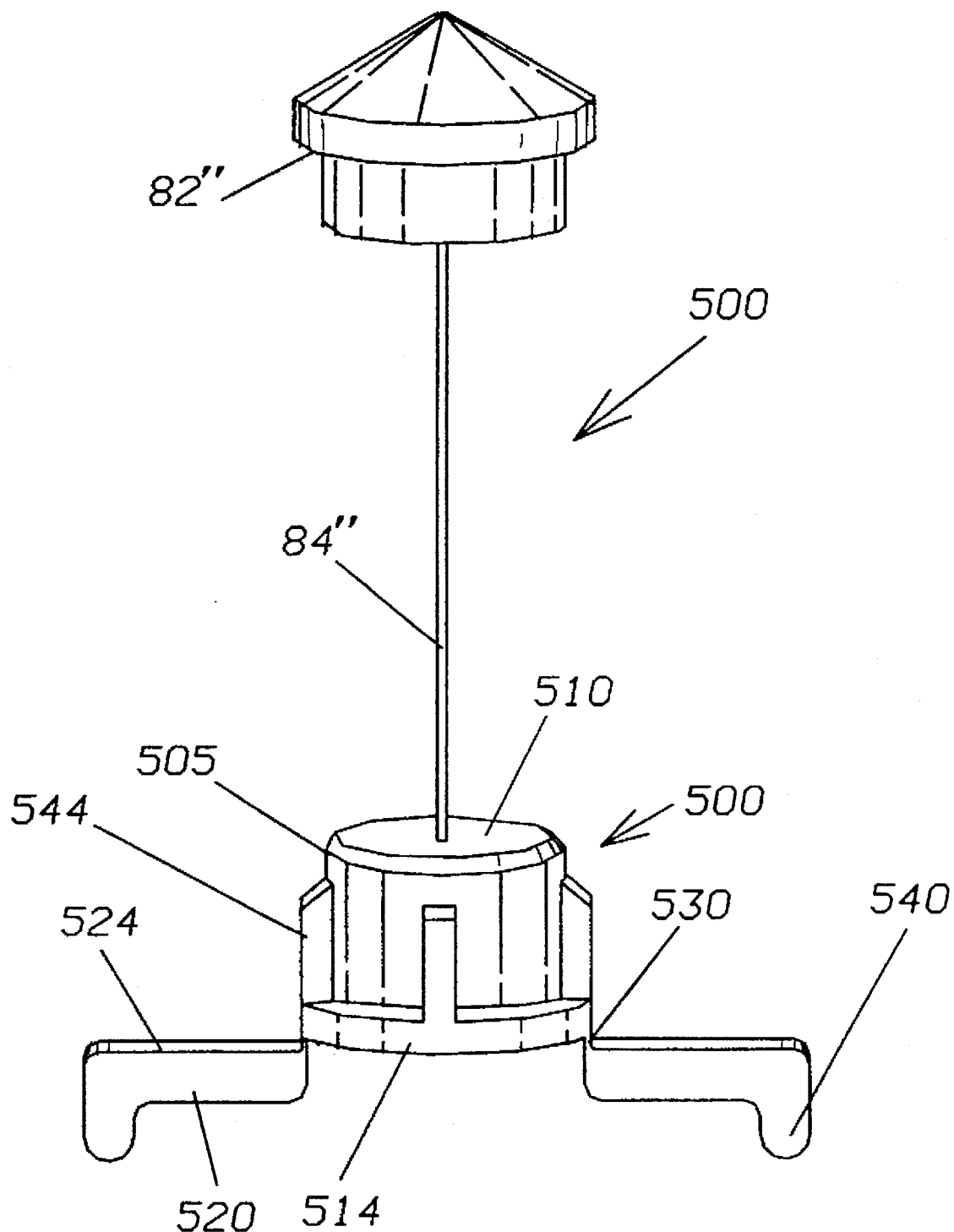
FIG. 22 is an enlargement of the tether structure of FIGS. 15–21.

The presently preferred embodiment for utilizing conventional syringe barrels is shown generally in FIGS. 15 and 16. The syringe 5" includes conventional syringe barrel 10" having a conventional main bore 22" which is preferably smooth and continuous in diameter throughout its length. The main bore 22" extends to distal tapered portion 14" and the bore is in fluid connection with a distal conduit 22" extending to distal tip 18". The syringe 5" further includes a main piston 38" connected by a flexible tether 84" to divider piston 58". The divider piston 58" contains a tether valve 500. The valve 500 includes a cylindrical plug 505 with upper surface 510. The plug 505 has a distal end 512 with an annular rim 514 for diverting flow, as will be described. The plug 505 is connected to two radially-projecting legs 520 having upper contact area 524 by flexure regions 530. The legs include extensions or feet 540 having a radius 544, the feet 540 project axially away from the legs 520. The plug 505 includes axial ribs 545 for providing an annular flow area and to guide and retain the plug 505 and to provide pulling engagement against the divider piston 58" when the tether 84" is retracted, as will be described. The plug 505 is connected to the tether 84", which is integral with the main piston retainer 82" for insertion and retention within the main piston 38". Generally, the structure of the reservoir divider 58" is similar to that described with the previously-discussed embodiment. However, the reservoir divider 58" with this embodiment includes a cylindrical central flow channel 550 having a smaller proximal bore 560 connected to a larger main bore 570. The bore is further connected to two axially-projecting slots 574 for receiving the legs 520. Four radial/circumferential slots or flow channels 758 are further provided in fluid communication with the main bore 570 for bi-directional flow and circumferential flush, as will be discussed. The reservoir divider 58" includes fulcrum point 580 for contacting leg contact area 524 and for inducing downward flexion of the legs 520 through pivoting action about the radius 544 of feet 540 when the divider piston 58" is advanced downwardly and the feet 520 are pressed against the tapered portion 14".

In assembly, the tether valve 500 is inserted the reservoir divider 58" by first inserting the tether 84" through the bores in the tether divider 58" and seating the legs 520 within the slots 574. The reservoir divider 58" is, with its associated tether valve 500, attached through the tether 84" to the main piston 58" is inserted into the bore 22 of the syringe 5 and advanced until the feet of the tether valve 500 contact the distal tapered portion 14 of the syringe 5. At this point, further pressure upon the upperface 72" of the reservoir divider 58" causes the fulcrum point 580 to induce downward flexion of the legs 540 around radius 544, thereby causing downward unseating deflection of the tether valve piston out of bore 560 and away from sealing contact with main bore 570. This opens fluid communication between the primary and secondary reservoirs 68 and 67.

Prior to operation, the main piston 38" is fully advanced, as described above, and the reservoir divider piston 58" is frictionally retained adjacent the distal end 14" with the tether valve plug 505 displaced downward from the seated position (as shown in FIG. 15). The syringe is operated in a similar manner to that described for the previous embodiments and may be used in the same environments within the hospital and in home patient care. Cannula 111" is initially placed in fluid connection with a source of flush solution (not shown) and handle 34" is retracted which withdraws the main piston 38", enlarging the primary reservoir 66". In response to the retraction of main piston 38", fluid enters the distal conduit 26" and passes through the radial/circumferential flow channels 758 through the central flow channel 550 and into the secondary reservoir 68". During this time, the reservoir divider piston 58" is frictionally held. When the primary reservoir 66" has been filled, the syringe 5" can then be connected to a second fluid source (or in the case of blood aspiration, may already be connected to a second fluid source, as previously described). The nurse then retracts the handle 34" farther. This causes the tether 84" to urge the plug 505 into the proximal bore 560 to occlude the proximal bore 560 so that primary reservoir 66" is isolated from the distal conduit 26". Further retraction withdraws the cylinder divider piston 58" away from the fully advanced position to enlarge the secondary reservoir 68". In response to enlargement of the secondary reservoir 68", fluid from the second fluid source enters the secondary reservoir 68". Once the secondary reservoir 68" has filled, the syringe 5" contains fluid from the first fluid source within the primary reservoir 66" and fluid from the second fluid source within the secondary reservoir 68". As with the previous embodiments, the nurse can then inject these fluids into the patient in the reverse order in which they were obtained. To perform this injection, for example, the nurse inserts the cannula into an I.V. access port (not shown) and advances the handle 34", which pushes the main piston 38" downward, increasing pressure within the primary reservoir 66". The hydraulic force within the primary reservoir 66" pushes the cylinder divider piston 58" downward since fluid cannot escape from the primary reservoir 66". Transmission of hydraulic force to the plug 505 is limited by the limited upper surface area of the plug 505, which can be reduced further than shown, so that the plug is not displaced from its seated position by the pressure within the primary reservoir 66". Complementary detents (not shown) along the plug 505 and bore 570 can be provided if additional retention security is desired. As the cylinder divider piston 58" advances, the fluid is injected into the patient from the secondary reservoir 68". When the secondary reservoir 68" is nearly empty, the feet 540 of the tether valve 500 contacts the tapered distal end 14" of the barrel 22", causing downward displacement of the plug 505 from the proximal valve bore 560, as previously described. This allows fluid to escape through the proximal bore 560 from the primary reservoir 66" into the secondary reservoir 68" to completely flush the secondary reservoir 68" and distal conduit 26". To provide a comprehensive flush of the flow space 116", flow is channeled through the main valve bore 570 which is occluded at its distal end by the annular rim 514 of the plug 505 to force the flow through the radial/circumferential slots 758 into the flow space 116", thereby creating a turbulent circumferential flushing action.

Figure 23:
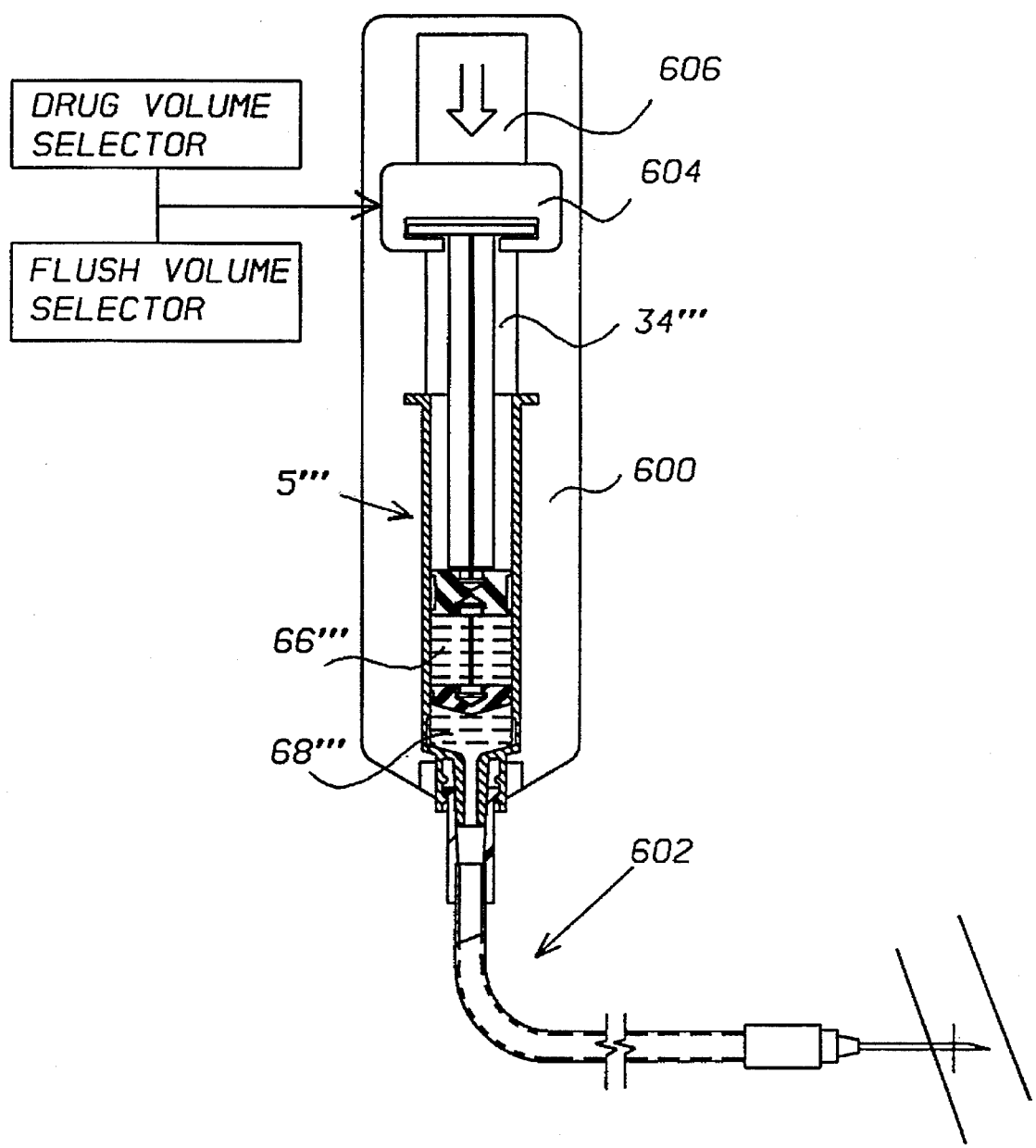
FIG. 23 shows a syringe in accordance with the invention incorporated in an automatic syringe pump.

FIG. 23 shows the sequential syringe 5'" incorporated into an automatic syringe pump 600. The syringe is in fluid connection with a conduit 602 for insertion into a blood vessel. The syringe handle 34'" is engaged, with handle holder 604 connected to pumping mechanism 606 for advancing the syringe handle 34'", as is known in the art. The syringe can include a mechanical or electronic volume-selector for selecting the specific drug solution volume and a selector for selecting a specific flush solution volume. Syringe pump 600 can include an algorithm for automatically adjusting for the flush volume contained within primary reservoir 66'" so that the nurse need not be concerned with selecting the specific flush volume within primary reservoir 66'". This is advantageous in reducing the work and concern of the nurse related to the flush volume. Syringes having specific volumes and incorporated into the syringe pump can include automatic adjustments for preset flush volumes related to the specific size of the syringe.

Many modifications can be made within the scope of this teaching. For example, with intermittent blood sampling, the force to overcome the detent 118 can be adjusted by the angle and height of the detent so that the vacuum from a conventional evacuated container will not overcome the detent 118 to positively prevent the resident fluid within the primary reservoir from being transferred. Other means for so restraining the further advancement of the cylinder divider piston 58 in response to insertion of the cannula into an evacuated container after the primary reservoir 66 has emptied can be provided. For example, detents (not shown) could be provided along the handle 34 to engage a complimentary detent (not shown) at the syringe barrel base to achieve such positionally activated restraint of further forward advancement of the handle. The vent portion can include other means for providing variance in shape or dimension between the wipers along the divider and the bore so that the tight seal is broken at the venting portion to form a flow channel between the reservoirs, or by otherwise providing a region adjacent the distal end wherein the bore shape changes in relationship to the divider so as to cause the divider to become free from tight-sealing contact with the bore. In such embodiments, it is preferable that the divider, when in the sealing contact with the bore. In such embodiments, it is preferable that the divider, when in the venting position, becomes free from tight-sealing contact in a nearly complete circumferential manner so that fluid may flow about the entire perimeter of the divider to completely flush any deadspace within the primary chamber and distal conduit free of residual blood or drug solution with a minimal amount of fluid. This is most important when the syringe is being used as part of a blood aspiration assembly for repetitive blood isolation since it is desirable to prevent blood from accumulating within the deadspace of the syringe. To achieve reduction in cost in molding the barrel of the syringe and to avoid providing the valve on the divider piston, the vent potion can be provided as a tapered circumferential expansion or undercut of the diameter of the bore adjacent the distal end and the wipers could be constructed to deflect when not tightly pressed against the bore within the expanded venting portion to allow fluid to escape around the wipers. A limited undercut may be achieved without the need for a collapsible core and, therefore, may substantially reduce the cost of molding. Such undercuts could also be used to provide the stops and seats of the syringe.

Other means for retracting the divider piston from the venting position can be provided. For example, the divider piston may be connected to the main piston by a flexible transparent chamber which can collapse when the main piston is advanced toward the divider piston when the flow channel is open. Furthermore, other means for providing a positionally-enabled and/or disabled fluid flow through a flow channel and valve mechanism may be provided including, for example, flap valves which allow flow into the primary reservoir, but which are closed by positive pressure in the primary reservoir. Such valves may be, for example, deflected open by pins when the pins contact the distal tapered end to allow the positive pressure to be released by expelling fluid past the deflected flaps. Other means for mechanically linking the main piston and divider piston will become evident to those skilled in the art and are included within the scope of this teaching. For example, although, as noted previously, a flexible tether is preferred, the linking or tensile element between the main piston and the divider piston can be either rigid or flexible. The linking element preferably directly connects the pistons through the element, but does not inhibit advancement of the main piston toward the divider piston when the flow channel is open and further allows independent retraction of the main piston with respect to the divider piston when the primary reservoir is incompletely fried. The linking element also preferably provides for mechanical combined mutually equivalent retraction of the main piston and the divider piston during retraction of the main piston after the primary reservoir has been fried. A rigid element which is connected distally to the divider piston and which telescopes through a bore in the main piston and which includes a proximal stop at a preset distance proximal to the main piston could provide a similar function to the preferred flexible linking element by allowing the rigid element to telescope through the main piston when the main piston is advanced, but causing retraction of the divider piston through retraction on the rigid linking element after the main piston is retracted such that it engages the proximal stop of the rigid element.

Although the presently preferred embodiments of this invention have been described, it will be obvious to those skilled in the art that various changes and modifications may be made therein without departing from the invention. Therefore, the claims are intended to include all such changes and modifications which may be made therein without departing from the invention. Therefore, the claims are intended to include all such changes and modifications that fall within the true spirit and scope of the invention.

We claim:

1. An automatic medical fluid injection assembly for the sequential injection of a first liquid and a second liquid, the assembly comprising:

a. a syringe defining a variable volume chamber having a distal end and an opening in said distal end, and further having an internal displacement volume and a piston to vary said internal displacement volume;

b. a chamber divider for separating said internal volume into at least proximal and distal variable volume reservoirs, said chamber divider being movable along said chamber, said proximal reservoir having a maximum volume;

c. a flow channel along said assembly, said flow channel being capable of providing flow connection between the proximal reservoir and the distal reservoir, said flow channel being in fluid communication with said conduit and said distal reservoir;

d. a valve capable of at least one disabling and enabling flow between said proximal reservoir and said distal reservoir through said flow channel;

e. an element for linking said piston and said chamber divider so that when said piston is moved away from said chamber divider, and said proximal reservoir is filled with said first liquid, said chamber divider is urged by said element away from said distal end of said chamber to enlarge said distal reservoir and to withdraw said second liquid into said distal reservoir;

f. said flow channel being sized and configured such that after said maximum volume of first liquid has been withdrawn into said proximal reservoir and said second liquid has been withdrawn into said distal reservoir, displacement of said maximum volume of first liquid through said flow channel is sufficient to displace all said second liquid from said syringe when said piston is advanced along said barrel;

g. automatic injection means, said injection means having means for automatically advancing said piston.

2. The assembly of claim 1, wherein said second liquid is a drug solution.

3. The assembly of claim 2, wherein said first liquid is a flush solution.

4. The assembly of claim 1, wherein said second liquid is blood.

5. The assembly of claim 4, wherein said first liquid is a flush solution.

6. The assembly of claim 5, wherein said automatic injection means further includes means for automatically sequentially injecting said second liquid followed by said flush solution, said second liquid comprising a specific volume of a drug solution, said automatic injection means including drug solution volume-selecting means for selectively injecting said specific volume.

7. The assembly of claim 5, further including flush solution volume selecting means for selectively injecting said maximum flush volume.

8. The assembly of claim 1, wherein said first liquid is a flush solution.

* * * * *